US011064960B2

(12) United States Patent
Jiang et al.

(10) Patent No.: US 11,064,960 B2
(45) Date of Patent: *Jul. 20, 2021

(54) SYSTEM AND METHOD FOR DIGITAL RADIOGRAPHY

(71) Applicant: SHANGHAI UNITED IMAGING HEALTHCARE CO., LTD., Shanghai (CN)

(72) Inventors: Jinpeng Jiang, Shanghai (CN); Yuyang Nie, Shanghai (CN); Zhongkun Guan, Shanghai (CN); Wei Wang, Shanghai (CN); Tao Ren, Shanghai (CN); Yun Cao, Shanghai (CN); Lin Ye, Shanghai (CN); Zhanqiang Kong, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 49 days.

This patent is subject to a terminal disclaimer.

(21) Appl. No.: 16/536,437

(22) Filed: Aug. 9, 2019

(65) Prior Publication Data
US 2019/0357864 A1    Nov. 28, 2019

Related U.S. Application Data

(63) Continuation of application No. 15/322,424, filed as application No. PCT/CN2015/091076 on Sep. 29, 2015, now Pat. No. 10,426,416.

(30) Foreign Application Priority Data

Sep. 29, 2014  (CN) .......................... 201420568992.3
Oct. 21, 2014  (CN) .......................... 201420609950.X
Aug. 11, 2015  (CN) .......................... 201510490957.3

(51) Int. Cl.
    A61B 6/00    (2006.01)
    A61B 6/04    (2006.01)
    (Continued)

(52) U.S. Cl.
    CPC .......... *A61B 6/4464* (2013.01); *A61B 6/0487* (2020.08); *A61B 6/102* (2013.01);
    (Continued)

(58) Field of Classification Search
    CPC ................ A61B 6/4464; A61B 6/0487; A61B 6/4482; A61B 6/589; A61B 6/588; A61B 6/4458;
    (Continued)

(56) References Cited

U.S. PATENT DOCUMENTS 5,426,683 A    6/1995 O'Farrell, Jr. et al.
5,768,336 A    6/1998 Khutoryansky et al.
(Continued)

FOREIGN PATENT DOCUMENTS

CN        1585227 A     2/2005
CN      200984237 Y    12/2007
(Continued)

OTHER PUBLICATIONS

Combined Search and Examination Report under Sections 17 and 18(3) in British Application No. 1902516.2 dated Apr. 26, 2019, 5 pages.
(Continued)

*Primary Examiner* — Courtney D Thomas
(74) *Attorney, Agent, or Firm* — Metis IP LLC

(57) ABSTRACT

The present disclosure relates to a system and method for digital radiography. The system may include an X-ray generation module, an X-ray acquisition module, a control module, a support module and a power supply module. The system may include one or more moving components. The X-ray acquisition module may have different configurations,
(Continued)

such as a vertical configuration, a horizontal configuration and a free-style configuration. The control module may be configured for controlling the motion of the moving components, the selection of an X-ray acquisition module of a specific configuration, and parameters of the X-ray exposure and image acquisition. The support module may include a system of guiding rails. The power supply module may include a supercapacitor.

20 Claims, 26 Drawing Sheets

(51) Int. Cl.
*A61B 6/10* (2006.01)
*H02J 7/34* (2006.01)

(52) U.S. Cl.
CPC .......... *A61B 6/4233* (2013.01); *A61B 6/4283* (2013.01); *A61B 6/4452* (2013.01); *A61B 6/4458* (2013.01); *A61B 6/4482* (2013.01); *A61B 6/467* (2013.01); *A61B 6/542* (2013.01); *A61B 6/545* (2013.01); *A61B 6/547* (2013.01); *A61B 6/548* (2013.01); *A61B 6/56* (2013.01); *A61B 6/587* (2013.01); *A61B 6/588* (2013.01); *A61B 6/589* (2013.01); *H02J 7/345* (2013.01)

(58) Field of Classification Search
CPC ....... A61B 6/587; A61B 6/542; A61B 6/4233; A61B 6/4283; A61B 6/548; A61B 6/545; A61B 6/467; A61B 6/102; A61B 6/4452; A61B 6/547; A61B 6/56; A61B 6/4405; H02J 7/345; H05G 1/10
See application file for complete search history.

(56) References Cited

U.S. PATENT DOCUMENTS

| | | | |
|---|---|---|---|
| 6,169,782 B1 | 1/2001 | Zetterlund | |
| 10,426,416 B2 * | 10/2019 | Kong | A61B 6/4283 |
| 2001/0012332 A1 | 8/2001 | Ertel | |
| 2005/0281377 A1 | 12/2005 | Heinze | |
| 2007/0253540 A1 | 11/2007 | Anderton et al. | |
| 2011/0243307 A1 | 10/2011 | Soto Santos | |
| 2012/0224673 A1 | 9/2012 | Barker et al. | |

FOREIGN PATENT DOCUMENTS

| | | |
|---|---|---|
| CN | 101399452 A | 4/2009 |
| CN | 201286709 Y | 8/2009 |
| CN | 201393172 Y | 1/2010 |
| CN | 201893599 U | 7/2011 |
| CN | 102611188 A | 7/2012 |
| CN | 202649777 U | 1/2013 |
| CN | 103207592 A | 7/2013 |
| CN | 203314986 U | 12/2013 |
| CN | 203458399 U | 3/2014 |
| CN | 103876759 A | 6/2014 |
| CN | 104144552 A | 11/2014 |
| CN | 203943682 U | 11/2014 |
| CN | 204016316 U | 12/2014 |
| CN | 204133487 U | 2/2015 |
| CN | 204145006 U | 2/2015 |
| CN | 204683628 U | 10/2015 |
| DE | 102010042565 A1 | 4/2012 |
| EP | 2351525 A2 | 8/2011 |
| GB | 745247 A | 2/1956 |
| JP | H0536491 A | 2/1993 |
| JP | H10116697 A | 5/1998 |
| JP | 3899862 B2 | 3/2007 |
| JP | 5621244 B2 | 11/2014 |
| WO | 2016050202 A1 | 4/2016 |

OTHER PUBLICATIONS

International Search Report in PCT/CN2015/091076 dated Jan. 12, 2016, 5 pages.
Written Opinion in PCT/CN2015/091076 dated Jan. 12, 2016, 7 pages.
Examination Report Under Section 18(3) in British Application No. 1902519.6 dated Jul. 9, 2019, 7 pages.
Examination Report in British Application No. 1902516.2 dated Jul. 5, 2019, 5 pages.
Combined Search and Examination Report under Sections 17 and 18(3) in British Application No. 1902519.6 dated May 1, 2019, 7 pages.

* cited by examiner

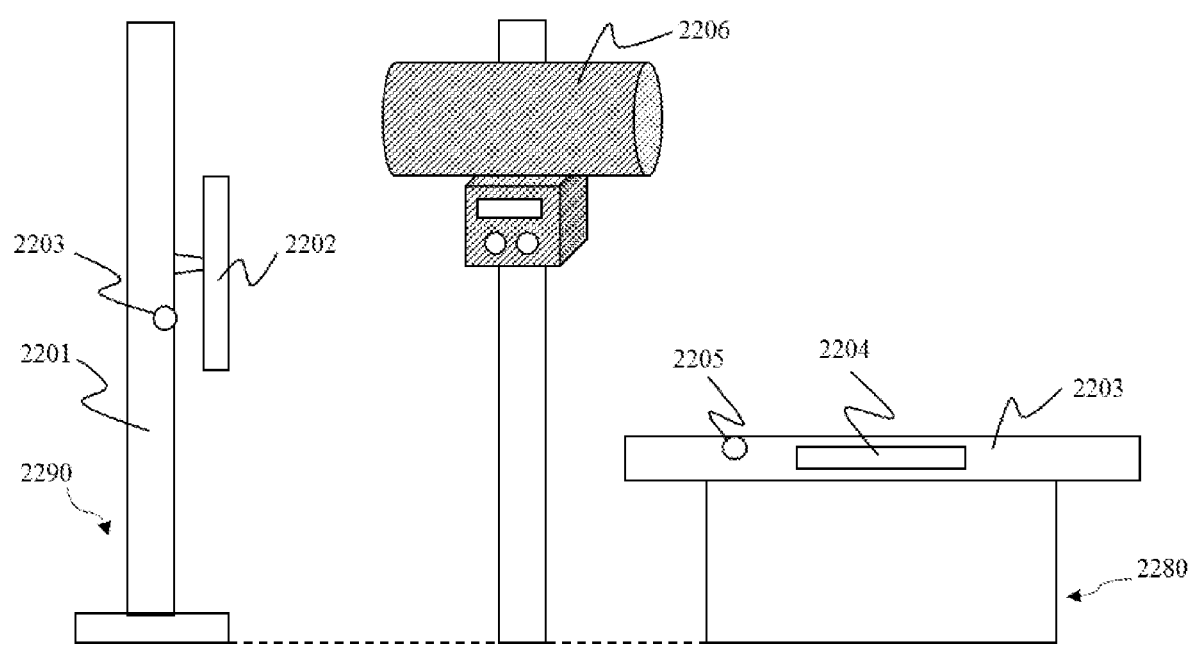
FIG. 2-A

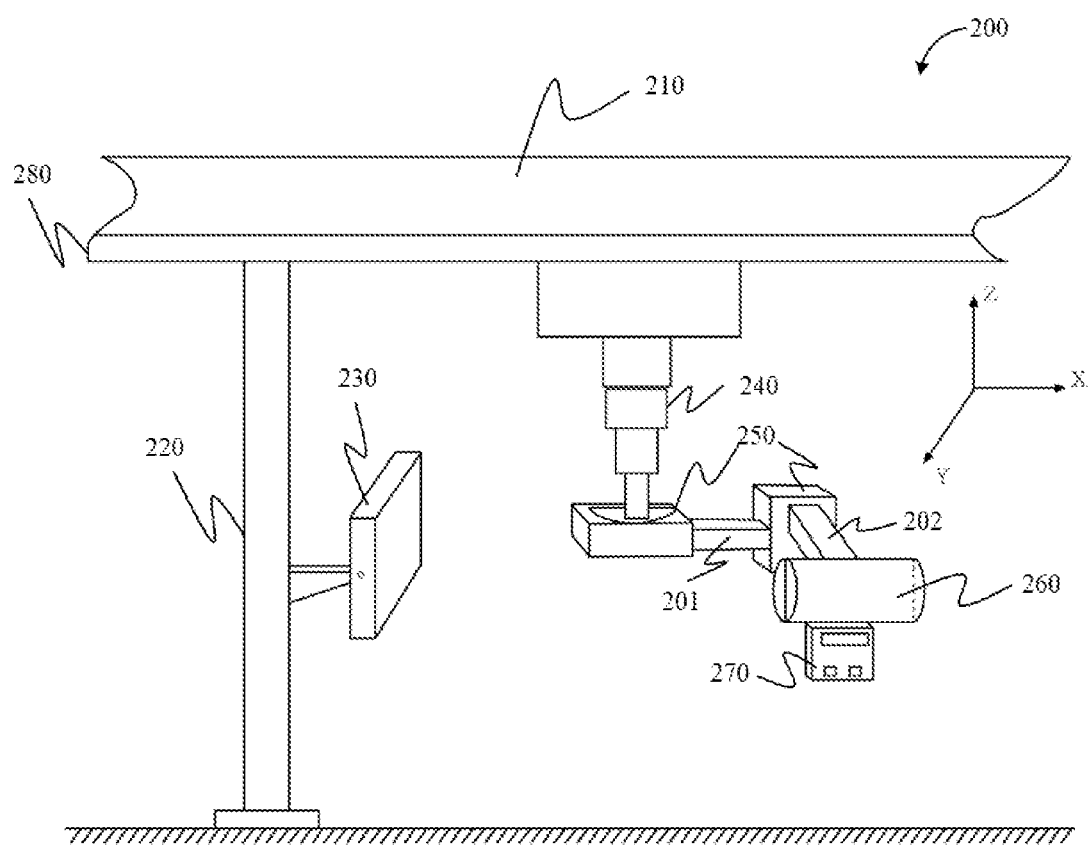
FIG. 2-B

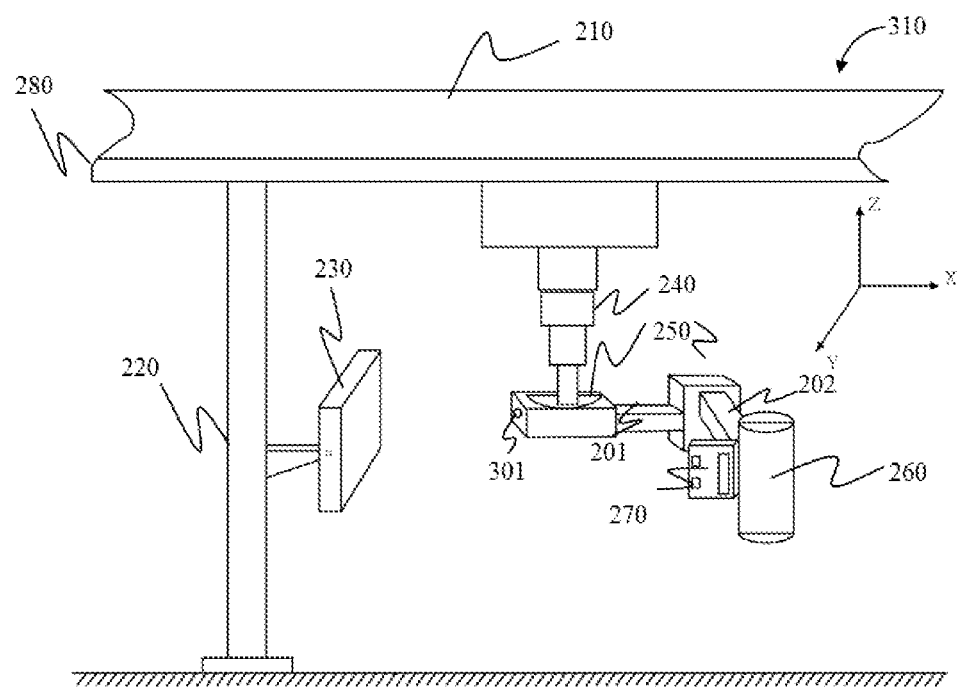
FIG. 3-A
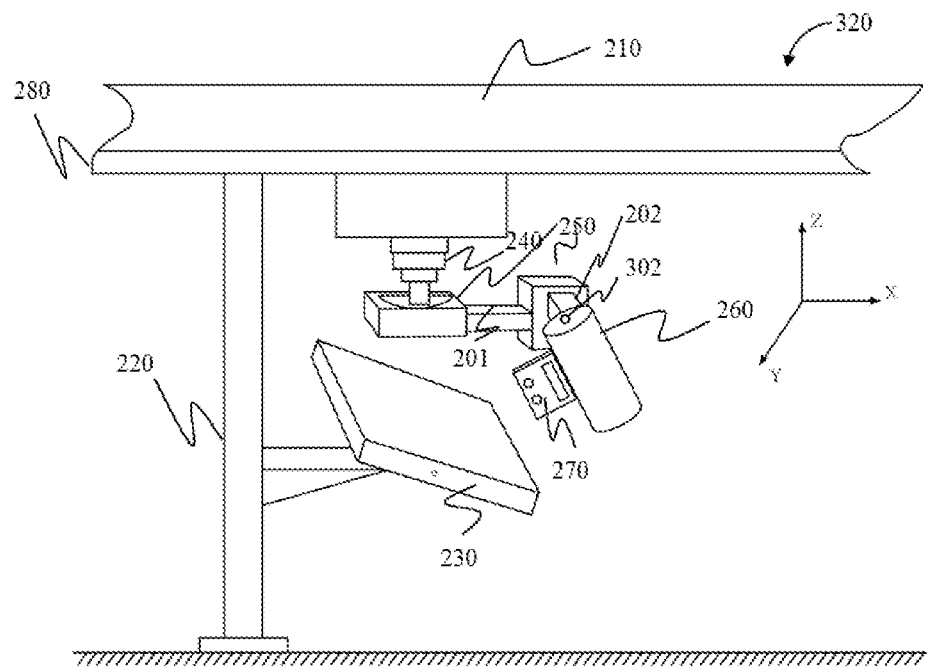
FIG. 3-B

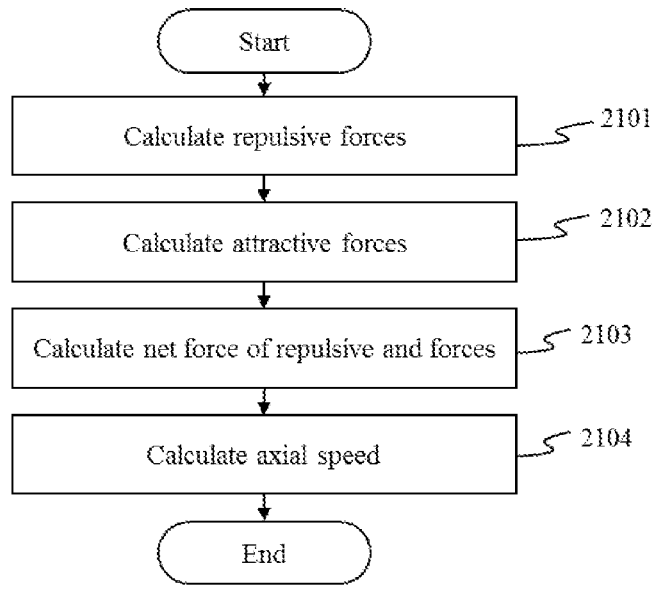
FIG. 21-A
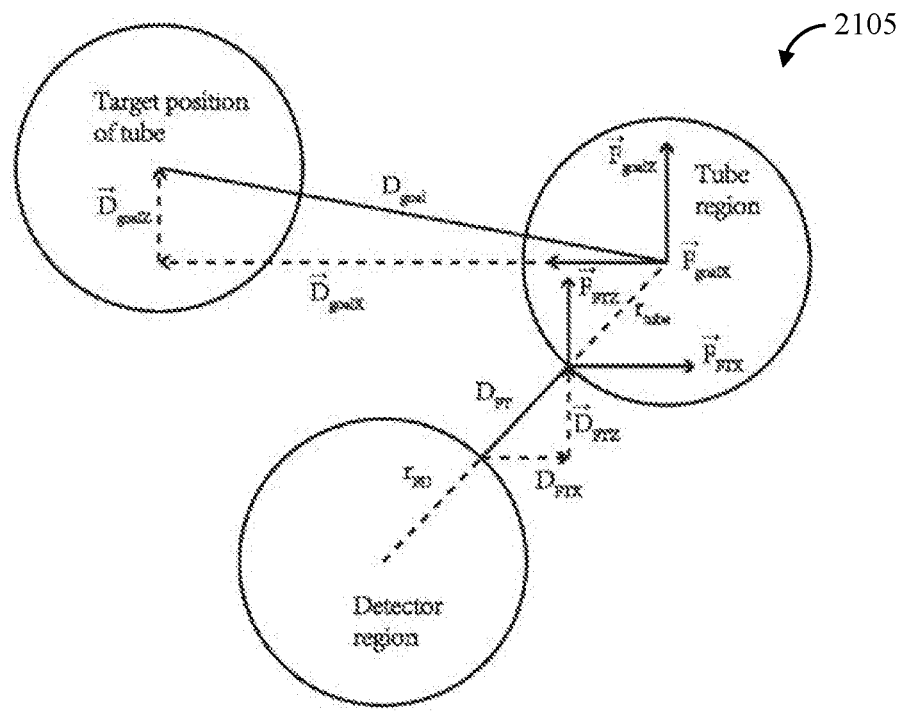
FIG. 21-B

SYSTEM AND METHOD FOR DIGITAL RADIOGRAPHY

CROSS-REFERENCE TO RELATED APPLICATIONS

This application is a continuation of U.S. application Ser. No. 15/322,424, filed on Dec. 27, 2016, which is a U.S. national stage under 35 U.S.C. § 371 of International Application No. PCT/CN2015/091076, filed on Sep. 29, 2015, which claims priority to Chinese Application No. 201420568992.3 field on Sep. 29, 2014, and Chinese Application No. 201420609950.X field on Oct. 21, 2014, and Chinese Application No. 201510490957.3 field on Aug. 11, 2015, each of which application is incorporated herein by reference in its entirety.

TECHNICAL FIELD

The present disclosure generally relates to a system and method for digital radiography imaging. Particularly, the present disclosure relates to a system and method for X-ray imaging.

BACKGROUND

Digital radiography (DR) is an advanced imaging technology, which combines the computer digital image processing and the X-ray emission technology. According to its advantages of low radiation doses, high image quality, high detection rate, and high accuracy, digital radiography has been widely used in many fields, such as aerospace, security, healthcare, etc. In medical digital radiography, X-ray signal is generated by a generator, and radiated to an imaging target such as a human body or other subjects. Then the X-ray signal can be detected by an X-ray detector, such as a flat panel detector. After a series of processes, an image of the radiated area can be formed, which may be used in disease diagnosis, medical research and other aspects.

SUMMARY

According to one aspect of the present disclosure, provided herein is a digital radiography system. Particularly, in some embodiment, the digital radiography system comprises an X-ray generation module, an X-ray acquisition module, a support module, a power supply module and a control module. In some embodiments, one or more of modules of the system comprise at least one moving component, the moving component comprising a sensing unit; the sensing unit is configured to obtain positional information of the moving component, and the control module is configured to control motion of the moving component based on said positional information.

In some embodiments, the positional information comprises distance between the moving component and a nearby object, and the control module further comprises a judgment unit capable of comparing the distance to a threshold; and the control module is configured to adjust speed of the motion, route of the motion or both, when the distance reaches the threshold.

In some embodiments, the moving component may be an X-ray detector, an X-ray tube, a ceiling suspension unit, a beam limiting device or a tube stand, and wherein the tube stand connects the X-ray tube and the ceiling suspension unit.

In some embodiments, the sensing unit is a photoelectric sensor or a linear proximity sensor.

In some embodiments, the control module digital radiography system further comprises a setting unit configured to set a target position for the moving component; a position unit configured to obtain instant position of the moving component and instant position of at least one obstacle; a calculation unit configured to calculate all axial speeds for the moving component, when the instant position of the moving component is different from the target position; and a control unit configured to move the moving component under the calculated axial speeds.

In some embodiments, the calculation unit calculates the axial speeds by determining a first collision area for the moving component and a second collision area for the obstacle; calculating a repulsive force by the obstacle; calculating an attractive force by the target position; calculating a net force of the attractive force and the repulsive force; and determining all axial speeds for the moving component.

In some embodiments, determining the first collision area and the second collision area is performed by finding a first rotating center of the moving component and a second rotating center of the obstacle; defining a first spherical space as the first collision area, the first spherical space having the first rotating center as spherical center, and the first spherical space enclosing the moving component; and defining a second spherical space as the second collision area, the second spherical space having the second rotating center as spherical center, and the second spherical space enclosing the obstacle.

In some embodiments, calculating the repulsive force is performed by calculating the repulsive force when $D_{FT} \leq D_{max}$. Particularly, $$\vec{F}_{FTX} = K_F \vec{D}_{FTX}/D_{FT}^2$$

$$\vec{F}_{FTZ} = K_F \vec{D}_{FTZ}/D_{FT}^2$$

where $D_{FT}$ is distance between the first collision area and the second collision area; $\vec{D}_{FTX}$ is X component of $D_{FT}$; $\vec{D}_{FTZ}$ is Z component of $D_{FT}$; $D_{max}$ is a threshold distance where the obstacle starts to exert the repulsive force; $\vec{F}_{FTX}$ is X component of the repulsive force; $\vec{F}_{FTZ}$ is Z component of the repulsive force; and $K_F$ is a proportionality coefficient.

In some embodiments, calculating the attractive force is performed by calculating the attractive force when $D_g \geq D_{min}$. Particularly, $$D_g = \begin{cases} D_{goal}(D_{goal} \geq D_{run}) \\ D_{run}(D_{goal} \leq D_{run}) \end{cases}$$

$$\vec{F}_{goalX} = K_g \vec{D}_{goalX} D_g / D_{goal}$$

$$\vec{F}_{goalZ} = K_g \vec{D}_{goalZ} D_g / D_{goal}$$

where $\vec{F}_{goalX}$ is X component of the attractive force; $\vec{F}_{goalZ}$ is Z component of the attractive force; Kg is a proportionality coefficient; $D_{min}$ is a threshold distance between the target position and the current position of the moving component; $D_{goal}$ is a distance between the target position and the current position of the moving component, $D_{run}$ is a minimum threshold for the attractive force; $\vec{D}_{goalX}$ is X component of $D_{goal}$; and $\vec{D}_{goalZ}$ is Z component of $D_{goal}$.

In some embodiments, determining all axial speeds for the moving component is performed by $$\vec{V}_x = \begin{cases} K_v \vec{F}_x & |K_v \vec{F}_x| \leq |\vec{V}_{maxX}| \\ \vec{V}_{maxX} & |K_v \vec{F}_x| > |\vec{V}_{maxX}| \end{cases}$$

$$\vec{V}_z = \begin{cases} K_v \vec{F}_z & |K_v \vec{F}_z| \leq |\vec{V}_{maxZ}| \\ \vec{V}_{maxZ} & |K_v \vec{F}_z| > |\vec{V}_{maxZ}| \end{cases}$$

where $\vec{V}_x$ is X axial speed; $\vec{V}_z$ is Z axial speed; $\vec{F}_x$ is net force in X axis; $\vec{F}_z$ is net force in Z axis; $K_v$ is transformation proportionality coefficient between force and speed; $\vec{V}_{maxX}$ is maximum speed in X axis; and $\vec{V}_{maxX}$ is maximum speed in Z axis.

In some embodiments, both the moving component and the obstacle are components of the digital radiography system. Particularly, in some embodiments, the obstacle is another moving component of the system.

In some embodiments, the system, when determining the motion path of a moving component, may treat another moving components of the system as an obstacle. For example, in some embodiments, the moving component is the X-ray acquisition module and the obstacle is the X-ray generation module. In some embodiments, the moving component is the X-ray generation module and the obstacle is the X-ray acquisition module.

In some embodiments, the X-ray acquisition module comprises a chest board enclosing the X-ray detector, and the X-ray generation module comprises the X-ray tube and the beam limiting device.

According to one aspect of the present disclosure, provided herein are device and method for path planning of an object with respect to an obstacle. Particularly, In some embodiments, the device comprises a setting unit configured to set a target position for the object; a position unit configured to obtain instant position of the object and instant position of the obstacle; a calculation unit configured to calculate all axial speeds for the object, when the instant position of the object is different from the target position; and a control unit configured to move the object under the calculated axial speeds.

In some embodiments, the method comprises setting an target position for the object; obtaining instant position of the object and instant position of the obstacle; determining a first collision area for the object and a second collision area for the obstacle; calculating a repulsive force by the obstacle; calculating an attractive force by the target position; calculating a net force of the attractive force and the repulsive force; and determining all axial speeds for the object.

According to one aspect of the present disclosure, provided herein are a digital radiography system comprising different configurations and a method for selecting among the configurations. Particularly, in some embodiments, one or more of modules of the system form a vertical configuration, a horizontal configuration and a free-style configuration; the vertical configuration comprises a vertical stand and a vertical X-ray acquisition module, the vertical X-ray acquisition module coupled to the vertical stand; the horizontal configuration comprises a bed component and a horizontal X-ray acquisition module, the horizontal X-ray acquisition module coupled to the bed component; the control module further comprises a detection unit configured to detect existence of an imaging target in one of the vertical and horizontal configurations; and the control module is configured to select the vertical or horizontal configuration based on the detected existence.

In some embodiments, the control module further comprises a timing unit configured to time the detected existence, and the control module is configured to select the vertical or horizontal configuration if the detected existence persists for a predetermined period of time.

In some embodiments, the vertical and horizontal X-ray acquisition modules each comprises an X-ray detector, an ionization chamber and a filter grid.

In some embodiments, the control module is further configured to activate the ionization chamber and the filter grid of the selected vertical or horizontal configuration.

In some embodiments, the control module is further configured to determine if the X-ray detector of the selected vertical or horizontal configuration is ready for image acquisition.

In some embodiments, the control module is further configured to select the free-style configuration if the existence of the imaging target is not detected.

In some embodiments, the detection unit is an infrared detector.

According to one aspect of the present disclosure, provided herein is a device for moving components of the digital radiography system. Particularly, In some embodiments, the system comprises a support beam having a length; the support beam comprises a first column, the first column having a first side along the length of the support beam; the support beam comprise a second column, the second column having a second side along the length of the support beam and a pair of opposing sides along the length of the support beam; the first side attaches to the second side and at least part of the first side is uncovered by the second side; the pair of opposing sides each comprises a prolonged guiding ridge along the length of the support beam; and the support beam further comprises a slider capable of engaging with the guiding ridges and moving along the length of the support beam.

In some embodiments, the support beam further comprises a housing between the second column and the slider, and wherein the housing encloses the second column.

In some embodiments, the slider is configured to connect a moving component of the system.

In some embodiments, the support beam further comprises a driving mechanism for moving the slider.

According to one aspect of the present disclosure, provided herein is an exposure controller for controlling generation and emission X-ray by the system. Particularly, In some embodiments, the exposure controller has a elongated handle, a double gear button and a switch, the elongated handle having a first end, a second end and a side; the double gear button is located on the first end of the handle, and the switch is located on the side of the handle.

In some embodiments, the exposure controller further comprises a protective groove and a movable baffle; the protective groove extends inwardly on the side of the handle; the switch is located within the groove; the movable baffle is configured to move between at least a first position and a second position; when the movable baffle is in the first position, the switch is accessible; and when the movable baffle is in the second position, the switch is inaccessible.

In some embodiments, the double gear button comprises a first gear and a second gear; the exposure controller is configured to send an exposure preparation signal to the X-ray generation module when the first gear is pressed; and the exposure controller is configured to send a first exposure permitting signal to the X-ray generation module when the second gear is pressed.

In some embodiments, the switch is configured to send a second exposure permitting signal to the X-ray generation module.

In some embodiments, the X-ray generation module is configured to generate X-ray when both the first and second exposure permitting signals are received.

In some embodiments, the exposure controller further comprises at least one audio device. In some embodiments, the audio device is a microphone. In some embodiments, the switch is a micro switch, a stir switch or a touch sense switch.

According to one aspect of the present disclosure, provided herein is a power supply system. Particularly, in some embodiments, power supply system comprises a power connector, a charge up circuit, a battery, a capacitor and a high-voltage generator; the power connector is configured to connect the charge up circuit to a power network; the charge up circuit is configured to supply power to the battery; the battery is configured to supply power to the capacitor; and the capacitor is configured to supply power to the high-voltage generator.

In some embodiments, the power supply system further comprises a current limiting charge up unit configured to supply power to the capacitor with a current limit.

In some embodiments, the power supply system comprises a power connector, a charge up circuit, a battery, a current limiting charge up circuit, a voltage limiting charge up circuit, a capacitor, and a high-voltage generator. Particularly, the power supply system is capable of selecting between at least a first circuit and a second circuit; in the first circuit, the power connector is configured to connect the voltage limiting charge up circuit to a power network; the voltage limiting charge up circuit is configured to supply power to the capacitor with a voltage limit; and the capacitor is configured to supply power to the high-voltage generator; and in the second circuit, the power connector is configured to connect the charge up circuit to the power network; the charge up circuit is configured to supply power to the battery; the battery is configured to supply power to the current limiting charge up circuit; the current limiting charge up circuit is configured to supply power to the capacitor with a current limit; and the capacitor is configured to supply power to the high-voltage generator.

In some embodiments, the power supply system is capable of selecting among at least the first circuit, the second circuit and a third circuit. Particularly, in the third circuit, the power connector is configured to simultaneously connect both the high-voltage generator and the charge up circuit to the power network; the charge up circuit is configured to supply power to the battery; the battery is configured to supply power to the current limiting charge up circuit; the current limiting charge up circuit is configured to supply power to the capacitor with a current limit.

In some embodiments, the power supply system further comprises a converter configured to convert one or more characteristics of the supplied power. In some embodiments, the converter is an AC/DC converter or a voltage transformer.

In some embodiments, the power supply system further comprises a battery level indicator configured to monitor a power level of the battery; and the battery level indicator is configured to stop power supply from the battery to the capacitor, when the power level of the battery decreases to a pre-determined battery level threshold.

In some embodiments, the power supply system further comprises a capacitor level indicator configured to monitor a power level of the capacitor; and the capacitor level indicator is configured to stop power supply from the capacitor to the high-voltage generator, when the power level of the capacitor decreases to a pre-determined capacitor power level threshold.

In some embodiments, the capacitor level indicator further comprises a calculation sub-unit configured to calculate a number of times the high-voltage generator can work until power in the capacitor runs out. In some embodiments, the capacitor level indicator further comprises a display sub-unit configured to display the calculated number.

In some embodiments, the power supply system is configured to automatically select the first circuit when power level of the battery is low. In some embodiments, the power supply is configured to manually select the second circuit.

BRIEF DESCRIPTION OF THE DRAWINGS

The present disclosure is further illustrated as exemplary embodiments. These exemplary embodiments are described in details with reference to the accompanying drawings. The drawings, which are incorporated in and constitute a part of this specification, illustrate several aspects described below. What illustrated in the drawings are non-limiting exemplary embodiments, in which like reference numerals represent similar structures throughout the several views of the drawings, and wherein:

FIG. 2-A provides an exemplary embodiment of a digital radiography system according to the present disclosure.

FIG. 2-B illustrates an exemplary embodiment of a digital radiography system according to the present disclosure.

FIG. 3-A and FIG. 3-B illustrate exemplary movement of system components of a digital radiography system according to the present disclosure.

FIG. 21-A is a flowchart illustrating exemplary path planning for the X-ray tube and X-ray detector according to the present disclosure FIG. 21-B is a diagram illustrating exemplary path planning for the X-ray tube and X-ray detector according to the present disclosure.

DETAILED DESCRIPTION

Figure 1:
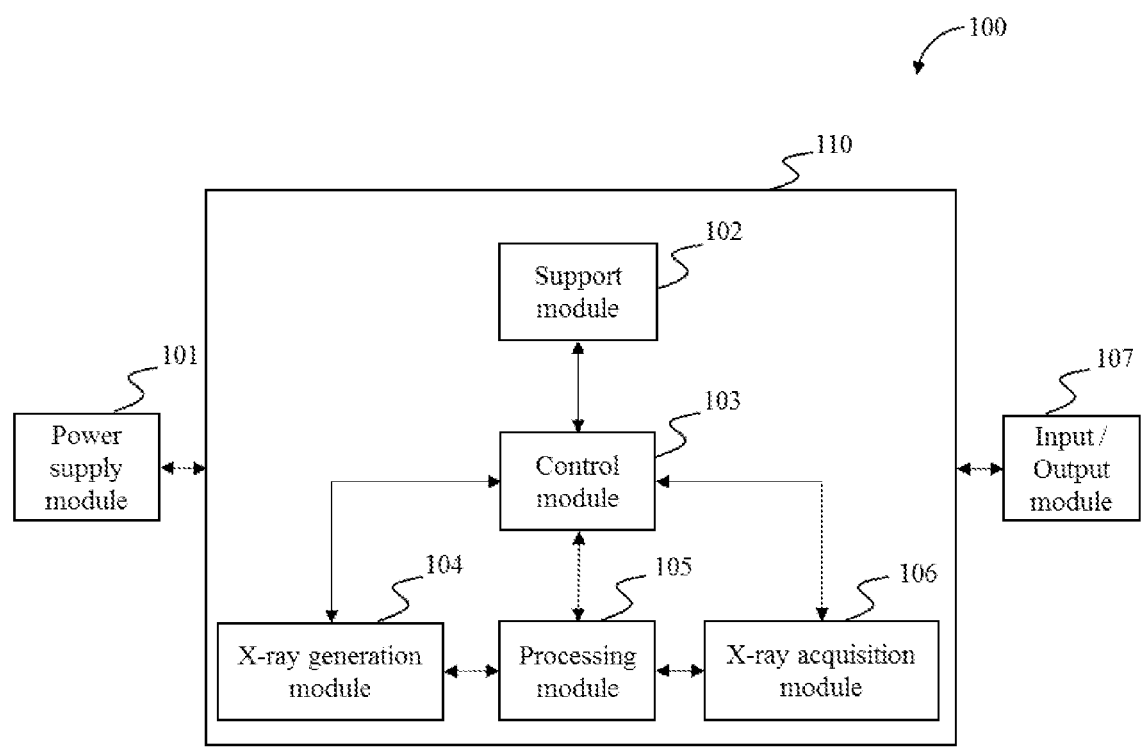
FIG. 1 illustrates an exemplary system diagram of a digital radiography system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) are for the purpose of illustration and description only and are not intended to limit the scope of the present disclosure. As used in the specification and in the claims, the singular forms of "a", "an", and "the" include plural referents unless the context clearly dictates otherwise.

After reading this description, it will become apparent to one skilled in the art how to implement the disclosure in various alternative embodiments and alternative applications. However, not all embodiments of the present disclosure are specifically described herein. It will be understood that the embodiments are presented by way of example only, and not limitation. As such, this detailed description of various alternative embodiments should not be construed to limit the scope or breadth of the present invention as set forth below.

According to one aspect of the present disclosure, provided herein are digital radiography systems. FIG. 1 illustrates an exemplary system diagram of a digital radiography system 100 according to some embodiments of the present disclosure. The digital radiography system 100 may include an operation module 110, a power supply module 101 and an input/output module 107. The operation module 110 may be configured to perform various operations of the system 100, including but not limited to controlling the position and movement of mechanical parts of the system and the generation of X-ray images. Particularly, as illustrated in FIG. 1, the operation module 110 may further include components for X-ray imaging of a target, including but not limited to an X-ray generation module 104, an X-ray acquisition module 106, and a processing module 105. The operation module 110 may also include mechanical parts for fixing, supporting, and/or moving the imaging components, which mechanical parts are collectively referred to as the support module 102 in the figure. The operation module 110 may further include a control module 103 that coordinates the operations and collaboration among different modules within the operation module 110, and/or between the operation module 110 and its peripheral devices, such as the power supply module 101, and the input/output module 107.

Particularly, the support module 102 may include any mechanical part that fixes, supports, and/or moves a component of the system. For example, in one embodiment, the support module 102 may include a vertical stand that fixes, supports and/or moves an X-ray acquisition device of the X-ray acquisition module 106 (A specific illustration of this embodiment is provided in FIG. 5). In another embodiment, the support module 102 may include a rail device or a ceiling suspension device for positioning and/or guiding the movement of an X-ray acquisition device of the X-ray acquisition module 106. In some embodiments, the X-ray acquisition device may be an X-ray tube, or an equivalent thereof. The structures and functions described above are not exhaustive and are not limiting; numerous other changes, substitutions, variations, alterations, and modifications may be ascertained to one skilled in the art and it is intended that the present disclosure encompasses all such changes, substitutions, variations, alterations, and modifications as falling within the scope of the appended claims. For example, in some embodiments, the support module 102 may be movable or non-movable. For example, in some embodiments, the support module 102 may have different shapes according to specific needs and/or for practical convenience.

The control module 103 may be configured for controlling the functions and operations of the system. The controlled function and operation may include moving and positioning a system component, such as moving an X-ray generation module 104 into close proximity of an imaging target, or adjusting an X-ray acquisition module 106 into an optimal angle with respect to the target, etc. Particularly, the control module 103 may calculate various preferred parameters, including but not limited to the route and speed of the movement, and execute the movement accordingly. More particularly, in some embodiments, the control module 103 may calculate the movement based on proximity sensing. Additionally or alternatively, the control module 103 may calculate the movement using an artificial potential field method. Further detailed disclosure regarding the artificial potential field method is provided in FIGS. 20 through 21 and related descriptions below.

Further, the controlled function and operation may also include the system's data acquisition, such as generating X-ray images of an imaging target. For example, the control module 103 may control the ON/OFF status of the X-ray generation module 104, control the ON/OFF status of power supply to the X-ray generation module 104, and calculate preferred parameters for X-ray generation and acquisition, etc. Particularly, in some embodiments, the control module 103 may control X-ray exposure conditions for image acquisition, execute or stop acquisition under a specific condition, and calculate preferred exposure parameters, etc. The control module 103 may include one or more control units (not shown in FIG. 1). In some embodiments, the control units (not shown in FIG. 1) may perform different control functions respectively. In some embodiments, the control units (not shown in FIG. 1) may perform one or more control steps sequentially or simultaneously.

The structures and functions described above in relation to the control module 103 are not exhaustive and are not limiting; numerous other changes, substitutions, variations, alterations, and modifications may be ascertained to one skilled in the art and it is intended that the present disclosure encompasses all such changes, substitutions, variations, alterations, and modifications as falling within the scope of the appended claims. For example, in some embodiments, the control module 103 may be integrated into the processing module 105 that executes the control functions directly. Alternatively, in other embodiments, the control module 103 may execute the control functions based on one or more instructions sent by the processing module 105. Yet alternatively, in some embodiments, the control module 103, some or all of the control units (not shown in FIG. 1) may be integrated into the X-ray generation module 104 or the X-ray acquisition module 106.

The X-ray generation module 104 may be configured for generating and/or emitting X-rays. The X-ray generation module 104 may connect to or otherwise communicate with the control module 103 and the processor 105. The X-ray generation module 104 may include one or more X-ray generation units (not shown in FIG. 1), such as an X-ray generation unit for generating a high voltage, an X-ray generation unit for monitoring the temperature in or around the X-ray generation module 104, an X-ray generation unit for emitting X-rays, or the like, or a combination thereof. In some embodiment, the X-ray generation module includes an X-ray tube and a high-voltage generator.

The processing module 105 may be configured to perform a plurality of operations during a running process of the system. The operations may include analysis, calculation, identification, or the like, or a combination thereof. The processor 105 may connect to or otherwise communicate with the X-ray generation module 104, the X-ray acquisition module 106 and the control module 103. The connection or the communication may be wired or may be wireless. The processing module 105 may include a digital signal processor (DSP), or a SoC (system on the chip), or a microprocessor, or the like, or the combination thereof. The processing module 105 may be integrated into another module within the operation module 110, or may be an independent component of the operation module 110. Additionally, each module in the operation module 110 may have its own independent processor. The processing module 105 may further include a cache memory (such as SRAM), which may be part of a memory hierarchy to store instructions and data. The processing module 105 may also include one or more logic modules (not shown in FIG. 1), such as a field programmable gate array (FPGA) or other logic array. The processing module 105 may perform functions according to instructions related to various modules or components of the system.

The X-ray acquisition module 106 may be configured for acquiring an X-ray signal relating to one or more imaging targets. The X-ray acquisition module 106 may be arranged on the support module 102 (such as a vertical stand). In some embodiments, the X-ray acquisition module 106 may be in either a vertical or horizontal arrangement with respect to the space where image acquisition takes place (such as an X-ray imaging room), or the imaging target (such as a patient). Alternatively, in other embodiments, the X-ray acquisition module 106 may assume any angle with respect to the imaging space or target. The X-ray acquisition module 106 may include one or more units (not shown in FIG. 1), such as an X-ray detector, a a chest board, an ionization chamber, a filter grid, or the like, or a combination thereof.

The structures and functions described above in relation to the operation module 110 are not exhaustive and are not limiting; numerous other changes, substitutions, variations, alterations, and modifications may be ascertained to one skilled in the art and it is intended that the present disclosure encompasses all such changes, substitutions, variations, alterations, and modifications as falling within the scope of the appended claims. For example, in some embodiments, the control module 103 is not needed, and, the X-ray generation module 104, the X-ray acquisition module 106 and the support module 102 may include one or more integrated control units (not shown in FIG. 1). Similarly, in some embodiments, the processing module 105 is not needed, and the various other modules may include one or more integrated processors. The connection or communication among the modules may be wired or wireless. The data or signal transmission may be in real time or with a time delay.

The power supply module 101 may be configured to supply power for one or more modules or components of the system. In some embodiments, the power supply module 101 may include a battery, such as but not limited to lithium battery, lead acid storage battery, nickel-cadmium battery, nickel metal hydride battery, or the like, or a combination thereof. In some embodiments, the power supply module 101 may include an external power source, such as but not limited to a power network with a household power outlet socket or industrial power outlet socket, or the like, or a combination thereof. The power supply module 101 may provide direct current (DC) power, or alternating current (AC) power. The power supply module 101 may include one or more internal components, including but not limited to a switch, a converter, a charge/discharge interface, or the like, or a combination thereof. Further detailed disclosure regarding the power supply module 101 is provided in FIGS. 12 through 17 and related descriptions below.

The input/output module 107 may be configured for inputting information related to the system, and/or outputting results generated by the system. The transmission of the input or output may be via a wired connection, or via a wireless connection. The input or output may be transmitted in real time, or may be transmitted with a time delay. The input or output may be in the format of, for example, a graph, a code, a voice message, text, video, an audio alert, a haptic effect, or the like, or a combination thereof. The input/output module 107 may be an input equipment, such as a keyboard, a mouse, a trackball, or cursor direction keys to convey information about direction and/or command selections to, for example, a processer. The input/output module 107 may be an output equipment, such as a display screen. Merely by way of example, the output may be displayed on a local terminal, or transmitted to a remote terminal, or both. A terminal may include, for example, a personal computer (PC), a desktop computer, a laptop computer, a smart phone, or a combination thereof.

FIG. 2-A provides an exemplary embodiment of a digital radiography system according to the present disclosure. As illustrated in FIG. 2-A, the digital radiography system may include both components for a vertical configuration 2290, and a horizontal configuration 2280. The system further includes an X-ray generation module 104, such as an X-ray tube 2206 as shown in FIG. 2-A.

Particularly, the vertical configuration components 2290 may include a vertical X-ray acquisition device 2202 installed on a vertical stand 2201. In various embodiments, the vertical X-ray acquisition device 2202 may include an X-ray detector, an ionization chamber, or a filter grid, or a combination thereof. The vertical X-ray acquisition device 2202 may move up and down the vertical stand 2201, thereby reaching an optimum location for X-ray image acquisition. For example, in some embodiments, a patient may stand in front of the vertical stand 2201. Thus, positions of the vertical X-ray acquisition device 2202 and the X-ray generation module 2206 may be adjusted according to the patient's position relative to the vertical stand 2201 as well as the body part to the imaged.

The horizontal configuration components 2280 may include a horizontal X-ray acquisition device 2204 installed on a bed component 2203. Similarly, the horizontal X-ray acquisition device 2204 may include an X-ray detector, an ionization chamber, or a filter grid, or a combination thereof. The horizontal X-ray acquisition device 2204 may move horizontally in the bed plane, thereby reaching an optimum location for X-ray image acquisition. For example, in some embodiment, a patient may lay flat on the bed component 2203. Thus, positions of the horizontal X-ray acquisition device 2204 and the X-ray generation module 2206 may be adjusted according to the patient's position relative to the bed as well as the body part to be imaged.

In some embodiment, the digital radiography system may detect the position of a patient or other imaging target, thereby detecting which of the vertical and horizontal configurations should be selected in the operation. Particularly, in some embodiment, the vertical configuration components 2290 further include a detection unit 2203, and the horizontal configuration components 2280 further include a detection unit 2205. In various embodiments, the detection units (2203, 2205) may be of the same type or different, such as an infrared sensor, or any sensor or sensing device that may be used for detecting an existence of an imaging target.

The structures and functions described above are not exhaustive and are not limiting; numerous other changes, substitutions, variations, alterations, and modifications may be ascertained to one skilled in the art and it is intended that the present disclosure encompasses all such changes, substitutions, variations, alterations, and modifications as falling within the scope of the appended claims. For example, the first detection unit 2203 and the second detection unit 2205 may be a detachable device which may be placed on any other particular component while needed. In another example, the first detection unit 2203 and the second detection unit 2205 may be controlled by a wireless remote tele-control device (such as an infrared remote controller).

In some embodiments, the digital radiography system may also include a free-style configuration, where the imaging components may assume any angle with respect to the imaging space or imaging target. FIG. 2-B illustrates an exemplary embodiment of the free-style configuration of the digital radiography system according to the present disclosure.

Particularly, as shown in FIG. 2-B, the digital radiography system may include a beam 210, a vertical stand 220, an X-ray detector 230, a ceiling suspension unit 240, a tube stand 250, an X-ray tube 260, a beam limiting device 270 and a moving guide 280.

In some embodiments, the vertical stand 220 may be installed on the ground plane parallel to the XY-plane in the three-dimensional coordinate system shown in FIG. 2-B. The X-ray detector 230 may be mounted upon the vertical stand 220. The X-ray detector 230 may rotate for certain angles in the three-dimensional space. The X-ray detector 230 also may move up-and-down along the vertical stand 220 in the Z-axis direction.

The X-ray tube 260 may be mounted on the tube stand 250, which in turn connects with the ceiling suspension unit 240. The beam limiting device 270 may be mounted proximal to the X-ray tube 260. The tube stand 250 may include a first stand unit 201 and a second stand unit 202. The first stand unit 201 may be at an angle with the second stand unit 202. For example, the first stand unit 201 may be perpendicular to the second stand unit 202. In some embodiments, the X-ray tube 260 and the beam limiting device 270 may rotate for a certain angle in the XY-plane and/or the XZ-plane in the three-dimensional space. In some embodiments, the tube 260 and the beam limiting device 270 may move in the Z-axis direction through the extension or retraction of the ceiling suspension unit 240. In some embodiments, the tube 260 and the beam limiting device 270 may move in the X-axis direction along the moving guide 280.

As will be further appreciated from FIGS. 3-A and 3-B and related descriptions below, movement of the system components may be controlled to ensure 1) various system components, including but not limited to components of the X-ray generation module 104 and X-ray acquisition module 106, are in optimum positions and angles relative to an imaging target to ensure satisfactory imaging effects, and 2) various system components will avoid accidental collision with other system components, objects external to the system, such as but not limited to an imaging target or imaging room furniture.

FIG. 3-A and FIG. 3-B illustrate exemplary movements of system components of the digital radiography system according to the present disclosure. As described in relation to FIG. 2-B, the components of the system may move and rotate in different directions or planes. In some embodiments, to avoid accidental collision and/or to ensure optimum position and angle of the components for imaging, a proximity sensing method is used. Particularly, in some embodiments, one or more proximity sensors may be placed on a moving component, such that sensing results, including but not limited the speed of moving, the distance or angle between the moving component and another proximate object may be sent to the control module 103. The control module 103 may then generate a motion control signal to avoid unwanted collision or fine-tune the position and angle of a system component. Particularly, proximate objects that may trigger the motion control signal may be other components of the system, or objects external to the system, such as the imaging target (e.g., a patient) or furniture within the imaging room. In various embodiments, the proximity sensor may be a photoelectric sensor, a infrared sensor, a linear proximity sensor, or any other type of sensor capable of sensing the existence of nearby objects.

For the convenience of illustration only, FIG. 3-A shows the situation where the tube stand 250 is arranged in an "L" shape; a first proximity sensor 301 is placed on the outer surface towards the X-ray detector 230. When the ceiling suspension unit 240 moves towards the X-ray detector 230, the proximity sensor 301 sends the sensing results (such as the distance remaining between the X-ray detector 230 and the outer surface of the tube stand 250) to the control module 103. When the sensing results reach a pre-set threshold value, the control module 103 may generate a motion control signal to, for example, slow down or stop the moving, change the route or tilt the angle of the movement of the ceiling suspension 240, etc.

Also for the convenience of illustration only, FIG. 3-B shows the situation where both the X-ray tube 260 and the X-ray detector 230 rotate in the three dimensional space. As shown in FIG. 3-B, a second proximity sensor 302 is placed on the outer surface of the X-ray tube 260. When the X-ray tube 260 rotates in the XY-plane, the second proximity sensor 302 may send the sensing results (such as the distance remaining between the X-ray detector 230 and the X-ray tube 260) to the control module 103. When the sensing results reach a pre-set threshold value, the control module 103 may generate a motion control signal to, for example, slow down or stop the moving, change the route or tilt the angle of the movement of the X-ray tube 260, etc.

The aforementioned motion control signal may be generated based on the sensing result and the threshold. For example, if the sensing result exceeds the threshold, a stop signal may be generated. If the sensing result is within a permissible range close to the threshold, a slow-down signal or a tilt signal may be generated.

In other embodiments, additional proximity sensors (not shown in FIG. 3) may be placed on various components of the system, including but not limited to the X-ray tube 260, the X-ray detector 230, the tube stand 250, the beam limiting device 270, etc. Particularly, one component may have multiple proximity sensors on a same or different surfaces. Also, the system may have close proximity sensors on more than one component simultaneously.

The structures and functions described above in relation to the proximity sensor are not exhaustive and are not limiting; numerous other changes, substitutions, variations, alterations, and modifications may be ascertained to one skilled in the art and it is intended that the present disclosure encompasses all such changes, substitutions, variations, alterations, and modifications as falling within the scope of the appended claims. For example, the multiple independent proximity sensors in the system may be replaced by a proximity sensor array. The proximity sensor array may include a series of sensors, arranged according to a specific rule.

Figure 4:
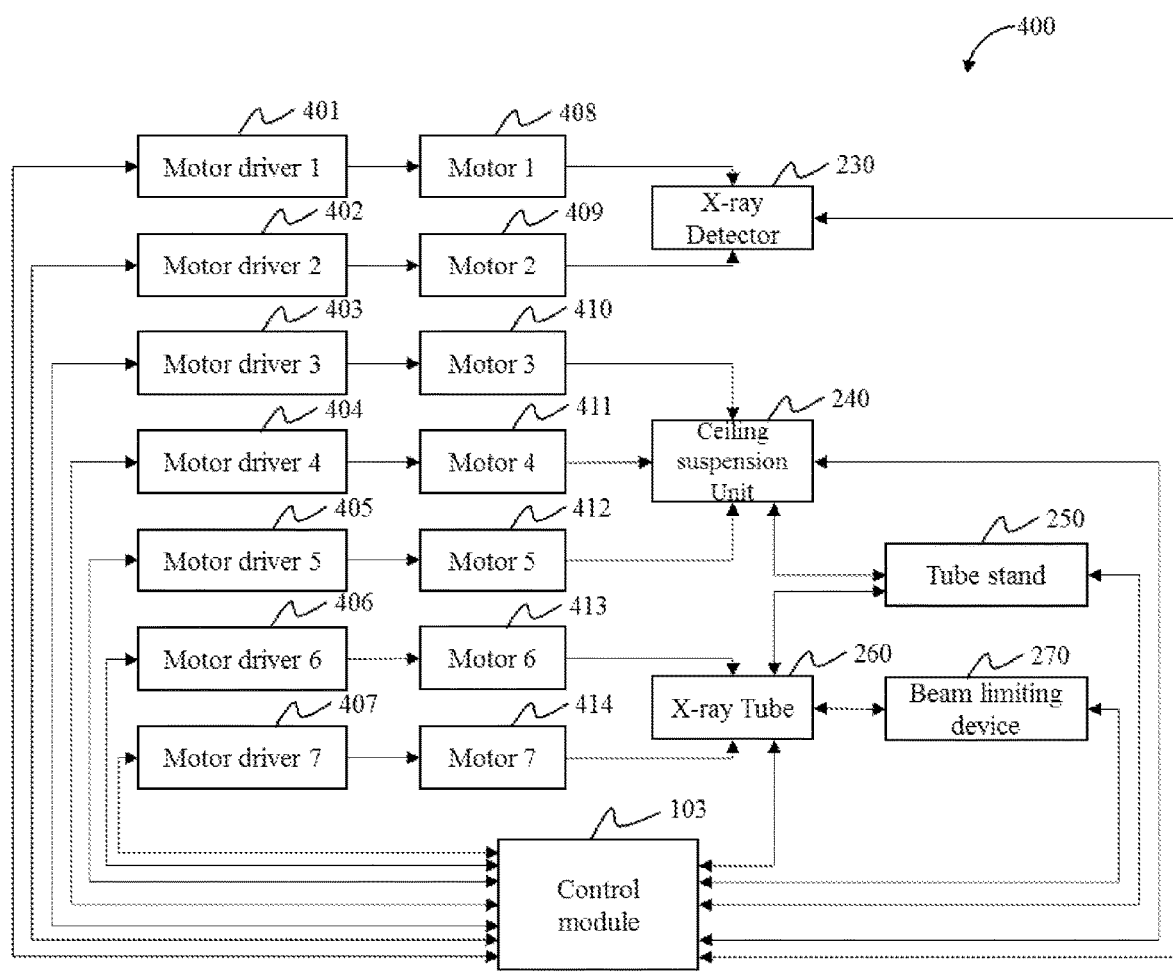
FIG. 4 is a block diagram illustrating an exemplary arrangement of some components in a digital radiography system according to some embodiments of the present disclosure.

FIG. 4 is an exemplary block diagram illustrating an arrangement of the components in the digital radiography system according to some embodiments of the present disclosure. As shown in FIG. 4, components of the system may be under direct or indirect control of the control module 103. The control module 103 may be configured for controlling one or more operations of the components, including movement and positioning of the components, parameters for an operation, or the like, or a combination thereof.

Particularly, as shown in FIG. 4, the control module 103 may coordinate movement of one or more system components through motors. Further, a motor may connect to a motor driver used for driving the motor. A component that can be moved in a controlled fashion may be any system module as depicted in FIG. 1 and related descriptions or any system component as depicted in FIG. 2 and related descriptions, which includes but is not limited to the X-ray detector 230, the ceiling suspension unit 240, the tube stand 250, the X-ray tube 260, the beam limiting device 270, or the like.

For example, as shown in FIG. 4, the tube stand 250 may connect to the ceiling suspension unit 240 and the X-ray tube 260 (see clear depictions in FIG. 2 and FIG. 3). The ceiling suspension unit 240 may connect to motor 3 410, motor 4 411 and motor 5 412, which motors may further connect to motor driver 3 403, motor driver 404 and motor driver 5 405, respectively. The X-ray tube 260 may connect to motor 6 413 and motor 7 414, which motors may further connect to motor driver 6 406 and motor driver 7 407, respectively. The X-ray detector 230 may connect to motor 1 408 and motor 2 409, which motors may further connect to motor driver 1 410 and motor driver 2 402, respectively. Further, as shown FIG. 4 the beam limiting device 270 may connect to the X-ray tube 260 and the control module 103.

The control module 103 controls and coordinates the movement of system components. As mentioned above, one or more proximity sensors may be used. For example, in some embodiments, the proximity sensor generates sensing results, which may include but are not limited to the speed or route information of the move, location and movement of other nearby objects, and remaining distance between the nearby objects and the moving system component, etc. The sensing results may be transmitted to an analysis unit (not shown in FIG. 4) in the control module 103. The analysis unit (not shown in FIG. 4) may be configured for providing an analysis result and comparing such result to a preset threshold.

As used herein, the preset threshold refers to a value corresponding to one or more parameter of an operation, and when the operational parameter approaches or reaches the threshold, the system will be triggered to act in response. Particularly, the threshold may be a single value or a value range. The system's reaction when a threshold is approached or reached may include but are not limited to stopping the operation, reversing the operation, adjusting one or more parameters of the operation, etc. The threshold may be set by the system default, or by a system operator, such as medical practitioners (e.g., a doctor) or other end users.

Take the operation of moving a system component as an example. A proximity sensor sends sensing results to the control module 103, which may include but are not limited to speed or route information of the move, location and movement of nearby objects, and remaining distance between the nearby objects and the moving system component. When, for example, the remaining distance approaches a preset distance value or falls within a preset distance range, the control module 103 may react by reducing the moving speed and/or tilting the moving angle of the moving system component and/or other moving object that controlled by the system. For example, when the remaining distance reaches a present distance value, the control module 103 may react by stopping or reverse the movement of the system component.

More particularly, referring to FIGS. 3-A and 3-B, multiple proximity sensors (e.g., 301, 302 in FIGS. 3-A and 3-B) may be placed on various moving system components. These proximity sensors provide information to the control module 103 for controlling and coordinating these movements and preventing accidental collisions between the system components, or between the system and an object external to the system, such as furniture or a patient.

In some embodiments, the control module 103 may include one or more control units (not shown in FIG. 4) that is a Field Programmable Gate Array (FPGA), a single chip controller, a microcontroller, or any processing or control component disclosed in the present disclosure, or the like, or a combination thereof.

The structures and functions described above in relation to the movement control are not exhaustive and are not limiting; numerous other changes, substitutions, variations, alterations, and modifications may be ascertained to one skilled in the art and it is intended that the present disclosure encompasses all such changes, substitutions, variations, alterations, and modifications as falling within the scope of the appended claims. For example, in some embodiments, separate control units may not be needed, as the control module 103 may be configured for performing the control function independently. In some embodiments, the control module 103 may be replaced by the processing module 105. In other embodiments, the control module 103 and the processing module 105 may be integrated into one independent module or an independent device that performs the control functions for the system.

According to one aspect of the present disclosure, provided herein is a system for moving system components to specific positions according to particular needs in practice.

Figure 5:
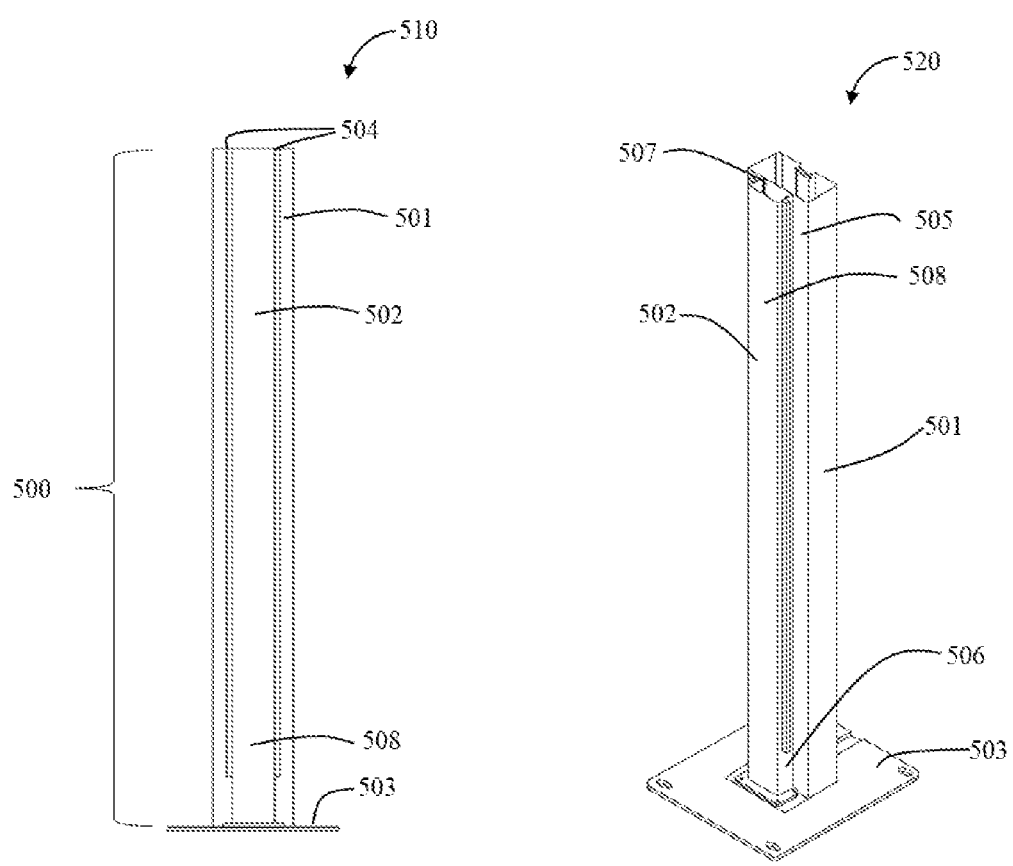
FIGS. 5 and 6 illustrate an exemplary embodiment of a support beam according to the present disclosure.
Figure 6:
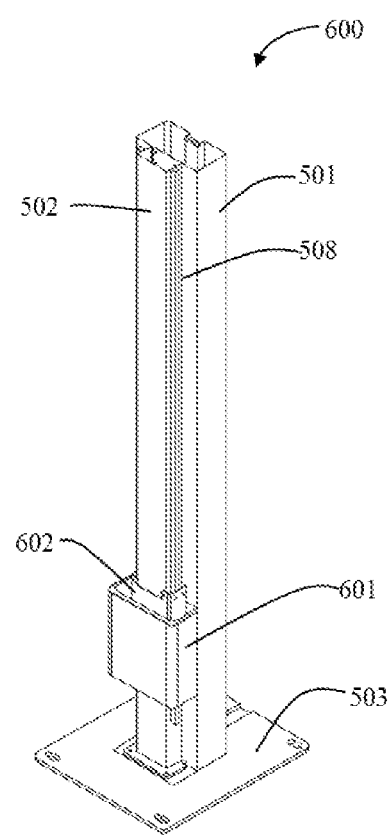

FIGS. 5 and 6 illustrate an exemplary embodiment of a support beam 500 according to the present disclosure. The left panel 510 shows the front view and the right panel 520 shows a perspective view of the support beam 500. As shown in the figure, in this embodiment, the support beam 500 includes a first column 501, a second column 502, and a pedestal 503. The first column 501 and the second column 502 are arranged adjacent to each other, the first column 501 having a larger cross section than the second column 502. Both the first column 501 and the second column 502 are fixed upon the pedestal 503. The second column 502 has two parallel guiding ridges 504 on its two opposing surfaces (506 and 507), respectively. Both guiding ridges 504 run along the length of the second columns 502.

As shown in FIG. 6, the support beam 500 may connect to a slider 601, which, upon engaging with the guiding ridges 504, may move along the length of the support beam 500, while the guiding ridges 504 serve as the rail for the sliding. In different embodiments, the guiding ridges 504 may have various different shapes, such as a rectangular guideway, round guideway, or dovetail guideway, or other configurations.

In some embodiments, the slider 601 may include sets of sliding wheels (not shown in FIG. 6) that engage with the guiding ridges 504 for the sliding. Particularly, in some embodiments, one set of sliding wheels may locate at each side of the slider 601 to engage with the two guiding ridges 504, respectively.

Additionally, to stabilize the sliding, such as preventing swaying of the slider 601 as it moves along the guiding ridges 504, additional sets of sliding wheels may be used. Particularly, in different embodiments, the slider 601 may include one or more additional sets of sliding wheels that run against surfaces of the first and second columns (501 and 502) to stabilize the sliding. Merely by way of example and not indented to be limiting, the one or more additional sets of sliding wheels may run against surface 505 of the first column 501, and/or surface 506, 507 and/or 508 of the second column 502.

In the above embodiments, each set of sliding wheels may include one or more rows of sliding wheels according to specific needs in practice. Yet, in other embodiments, sliding wheels may not be needed for the sliding. Alternatively, in those embodiments, the slider 601 may include sliding surfaces which substitute the function of sliding wheels to engage the guiding ridges 504 and/or stabilize against the column surfaces (e.g., 505, 506, 507, 508, etc.) for the sliding.

As shown in FIG. 6, the slider 601 may optionally include a cavity 602 between its outer surface and the portion adjacent to the second column 502. The cavity 602 may have a "U" shape in a cross section. The cavity 602 is not a required structure of the slider 601. Other structural modifications may be acceptable, as long as the slider 601 may move along the length of the support beam 500.

In some embodiments, the support beam may further include a driving mechanism for moving the slider. For example, in some embodiments, the support beam 500 may include a motor. Particularly, in those embodiments where the support beam 500 is used to move system components vertically, the support beam 500 may further include a matching weight unit such that the motor only needs to exert a relatively small force for elevating or lowering the system component.

Figure 7:
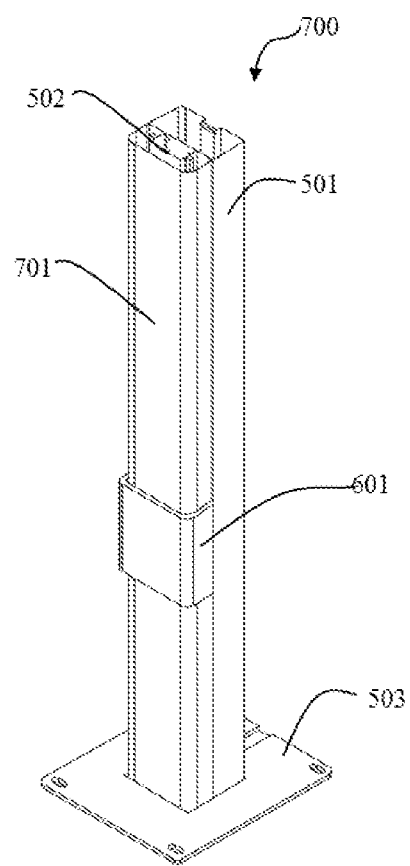
FIG. 7 illustrates an exemplary embodiment of a support beam according to the present disclosure.

FIG. 7 illustrates a different embodiment of the support beam 500. Particularly, in this embodiment, the slider 601 includes a "U" shaped cavity (see 602 in FIG. 6) and the support beam 500 further includes a housing 701. The housing 701 is placed between the second column 502 and the cavity 602. In this particular embodiment, the housing 701 also has a "U" shape in a cross section. Yet, in other embodiments (not shown), the shape of the cavity 602 and the housing 701 may be different. The second column 502 and the guiding ridges 504 may be enclosed within the housing 701. In this embodiment, the width of the housing 701 is the same as that of the first column 501. Yet, in other embodiments (not shown), the width of the housing 701 and the first column 501 may be different. The housing 701 protects the columns (501, 502), guiding ridges 504, sliding wheels (not shown) etc. from environmental impact, such as dirt, moisture, mechanic forces, etc. More detailed descriptions of the columns (501, 502) and guiding ridges 504 may be found in FIGS. 5 and 6 and related descriptions above.

Figure 8:
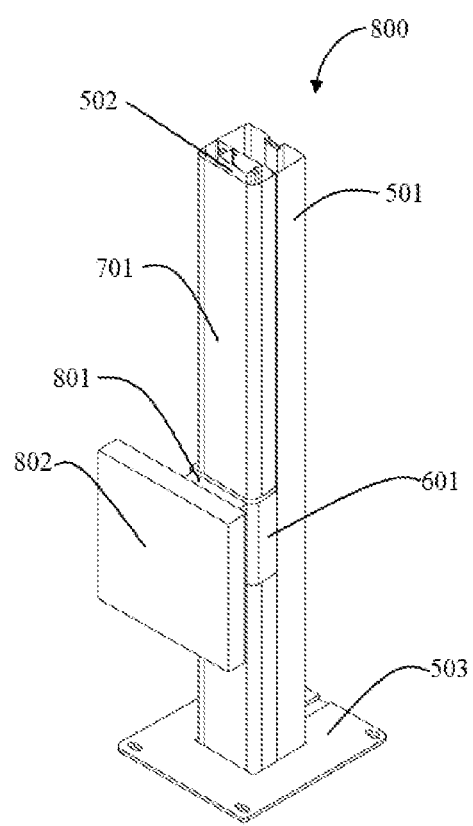
FIG. 8 illustrates an exemplary embodiment of a support beam according to the present disclosure.

FIG. 8 shows yet another embodiment of the support beam 500. Particularly, in this embodiment, the support beam 500 further includes a supporter 801. The supporter 801 connects to the slider 601, and may further connect to one or more system component 802 of the digital radiography system. For example, the system component 802 may be an X-ray acquisition module component, such as but not limited to a vertical chest X-ray detector, an image intensifier, optical lens, or the like, or a combination thereof. In other examples, the system component 802 may be an X-ray generation module component, such as but not limited to an X-ray tube, a beam limiting device, a tube stand, or the like, or a combination thereof. In yet further examples, the system component 802 may be any component of the digital radiography system, according to specific needs in practice.

In some embodiments the support 801 may not be needed, as the system component 802 may connect to the slider 601 directly. In other embodiments, the slider 601 may connect to an object external to the system, such as an imaging target. As such, the support beam 500 may be used to move and position a system component 802 or other objects to a particular location for image acquisition. More detailed descriptions of the support beam 500 and the slider 601 may be found in FIGS. 5, 6 and 7 and related descriptions above.

Further, it should be noted that although FIGS. 5 through 8 show the support beam 500 in a vertical fashion, the support beam 500 may be arranged in any direction within a three-dimensional space according to specific needs in practice. For example, in one embodiment, the support beam 500 can be used as the vertical stand 220 in FIGS. 2-3. Particularly in this embodiment, the first column 501 and the second column 502 are perpendicular to the pedestal 503; the pedestal 503 is fixed to the ground plane, such that the support beam 500 stands vertically in the three-dimensional space of the X-ray imaging room, and thus is capable of moving system components vertically within the room. Yet, in other embodiments, the support beam 500 may run in any direction with respect to the imaging room; that is, the support beam 500 may assume 0 to 90 degree angle with the X-Y plane (ground plane), the Y-Z plane or the X-Z plane in the X-ray imaging room, and thus is capable of moving system components in any of these directions the support beam 500 extends. Further, multiple support beam 500 may be organized together in a three-dimensional space, such that possible directions of movement are diversified. Yet further, in some embodiments, the support beam 500 may be curved or circular. In some embodiments, the support beam 500 may include a multiple sections, each section being straight, curved or circular.

The structures and functions described above in relation to the support beam 500 are not exhaustive and are not limiting; numerous other changes, substitutions, variations, alterations, and modifications may be ascertained to one skilled in the art and it is intended that the present disclosure encompasses all such changes, substitutions, variations, alterations, and modifications as falling within the scope of the appended claims. For example, in some embodiments, the second column 502 may be a bulge forming on the surface 505 of the first column 501. The method for connecting the first column 501 and the second column 502 includes but is not limited to riveting, soldering, fixing screws, integral forming, or the like, or a combination thereof. The method for connecting the guiding ridges 504 and the second column 502 includes but is not limited to riveting, soldering, fixing screws, integral forming, or the like, or a combination thereof. The method for connecting the system component 802 and the support component 801 includes but is not limited to riveting, soldering, fixing screws, integral forming, or the like, or a combination thereof. The support beam 500 may be made of metal materials (such as aluminum, steel, etc.), non-metallic materials, metamaterials or the like, or a combination thereof. The material of the first column 501 and the second column 502 may be the same or different. The shapes of the first column 501 and the second column 502 may be the same or different, which include but are not limited to rectangular, round, polygon, irregular shape, or the like, or a combination thereof. The slider 601 may be made by soldering materials which include but are not limited to aluminum, steel, metal plate, or the like, or a combination thereof. The housing 701 may be made by bending materials which include but are not limited to aluminum, steel, metal plate, or the like, or a combination thereof.

According to one aspect of the present disclosure, the digital radiography system may further include an exposure controller for an end user to control and operate the system more easily and conveniently. The exposure controller provides a hardware controlling mechanism that may either supplement or replace a software controlling mechanism of the system, thereby increasing safety.

Figure 9:
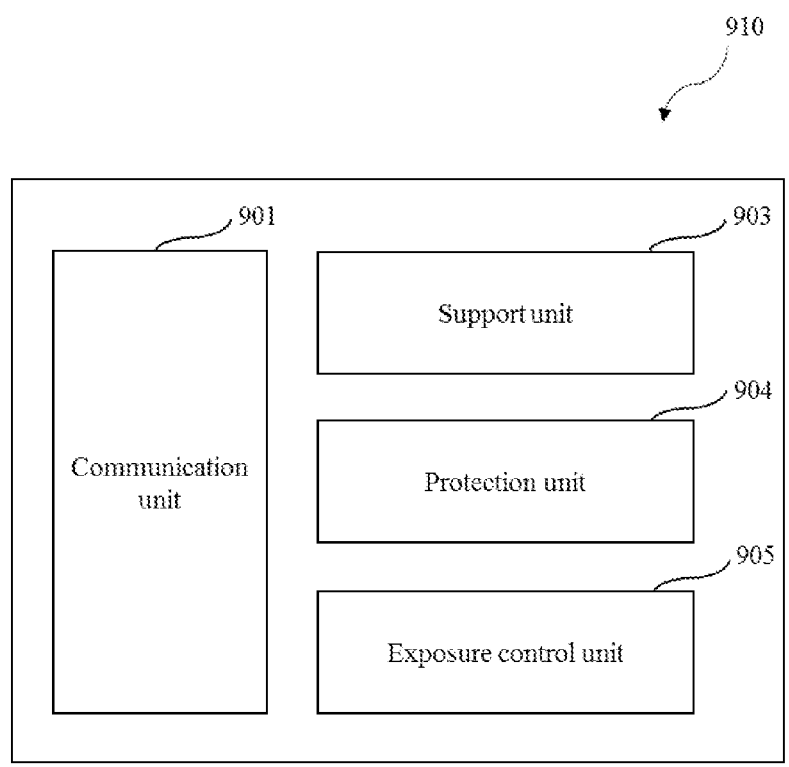
FIG. 9 illustrates exemplary functional units of an exposure controller according to several embodiments of the present disclosure.

FIG. 9 illustrates exemplary functional units of the exposure controller 910 according to several embodiments of the present disclosure.

Referring to FIG. 9, the exposure controller 910 may include one or more communication unit 901, support unit 903, protection unit 904, exposure control unit 905, and other suitable units.

In some embodiments, the communication unit 901 may enable communication 1) between the exposure controller 910 and other modules or components of the system (such as those control generation and emission of X-ray in the system); or 2) between the exposure controller 910 and an end user; or 3) between different end users. As used herein, an end user of the digital radiography system generally refers to any human subject that operates (such as a medical practitioner) or being examined by the system (such as a patient). Communications via the communication unit 901 may be in a wired and/or wireless fashion, and may include, for example, audio communications, video communications, mechanical contact, and other suitable types. For example, an end user may send commands to the system via the exposure controller 910, such as by providing a body gesture (such as pressing a button or stomping a foot paddle, etc.) or a voice command, etc. Further, an end user may communicate with another end user via the exposure controller 910.

The support unit 903 generally refers to any mechanical component of the exposure controller 910, such as but not limited to a handle, a paddle, a button, a switch, a protecting case, etc.

In some embodiments, the protection unit 904 functions to prevent accidentally sending undesired commands to the system by error triggering. For example, in the field of digital radiography, a situation that the protection unit 904 aims to prevent would be accidentally or erroneously triggering the system to emit X-ray when a patient, a medial practitioner and/or another system component is not yet ready for X-ray image acquisition. In some embodiments, the exposure control unit 905 functions to monitor and control radiation emission by the digital radiography system. For instance, the exposure control unit 905 may control the ON/OFF status of X-ray emission, as well as the intensity and duration of X-ray emission.

As can be appreciated from further detailed descriptions of specific embodiments of the exposure controller 910, function-wise, the aforementioned functional units (901, 903, 904, 905) work in concert to enable safe and convenient operation of the system by an end user. Yet, structure-wise, these functional units may each has its own independent hardware components or share one or more common hardware components.

Figure 10:
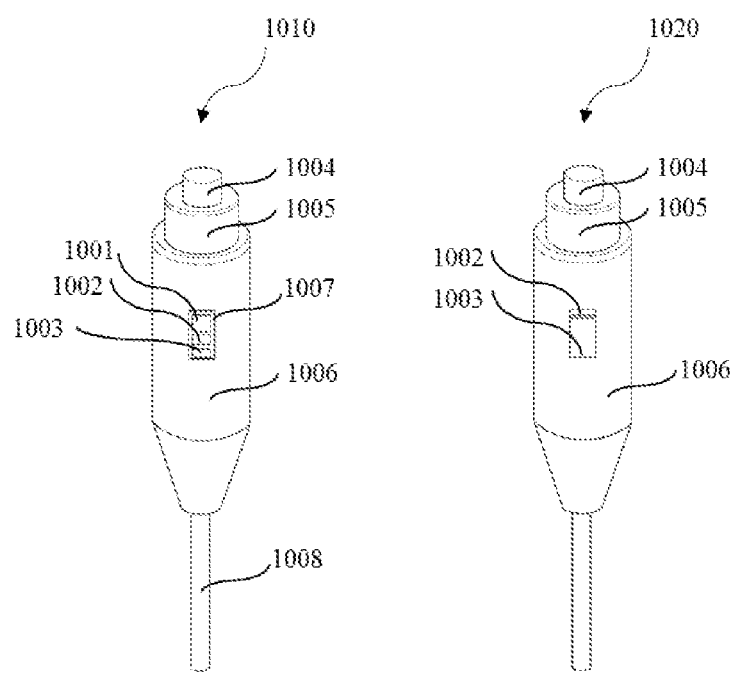
FIG. 10 illustrates an exemplary embodiment of an exposure controller according to the present disclosure.

FIG. 10 illustrates an exemplary embodiment of the exposure controller 910 according to the present disclosure.

Referring to FIG. 10, in this particular embodiment, the exposure controller 910 includes a handle 1006, a double gear button having a first gear 1004 and second gear 1005, a protective groove 1007, a movable baffle 1003 with a handgrip 1002, a switch 1001, and a signal line 1008. Particularly, the handle 1006 assumes an elongated shape; the double gear button (1004, 1005) locates on one end of the handle 1006. The other end of the handle 1006 connects to the signal line 1008. The protective groove 1007 extends inwardly on the side of the handle 1006, forming a bottom face (not shown in FIG. 10) and at least two opposing side faces (not shown in FIG. 10); the switch 1001 locates within the groove 1007.

The movable baffle 1003 may move relatively to the protective groove 1007, and has at least two positions. Left panel 1010 illustrates the first position of the movable baffle 1003 relative to the protective groove 1007; in the first position, at least part of the protective groove 1007 is exposed and an end user may access the switch 1001. Right Panel 1020 illustrates the second position of the movable baffle 1003; in the second position, the groove 1007 is enclosed by the movable baffle 1003, and an user cannot access the switch 1001. In some embodiments, the protective groove 1007 has indentations (not shown in FIG. 10) along its side faces, and the movable baffle 1003 may slide within those indentations between the first and second positions. Alternatively, in other embodiments, sliding rails (not shown in FIG. 10) may be positioned on the outer surface of the handle 1006 near the protective groove 1007, and the baffle 1003 may slide along those sliding rails between the first and second positions. In some embodiments, the movable baffle 1003 may have a handgrip 1002, such that a user may push the movable baffle 1003 more easily between the first and second positions.

When in use, this embodiment of the exposure controller 910 provides several safety features to prevent accidentally or erroneously triggering X-ray exposure. Particularly, in some embodiments, an end user need to both turn on the switch 1001 and press down the double gears (1004 and 1005), in order to trigger X-ray exposure. Specifically, for a user to access the switch 1001, the movable baffle 1003 needs to be at the first position. In some embodiments, the movable baffle 1003 is configured to 1) stay in the second position until a user moves it, and 2) return to the second position after the user release it. Thus, in these embodiments, the user always needs to go through the step of moving the baffle 1003 before activating X-ray exposure.

Additionally, in some embodiment, the switch 1001 may be an auto-lock switch. In these embodiments, a user needs to press the switch 1001 once to turn it ON, and press again to turn it OFF. In other embodiments, the switch may be a self-reset switch. Particularly, in these embodiments, the user needs to press and hold the switch 1001 to turn it ON, and the switch 1001 automatically turns off when released. Thus, in these embodiments, the user always need to go through the step of turning on the switch 1001 before activating X-ray exposure. Particularly, in those embodiments where the switch 1001 is a self-reset switch, the user further needs to press and hold it to complete X-ray exposure.

Further, in some embodiments, a user need to press down both gears (1004, 1005) to activate X-ray exposure. Particularly, in some embodiments, when the user presses down the first gear 1004, the exposure controller 910 sends a preparation signal to the X-ray generation module 104; when the user presses further down to the second gear 1005, the exposure controller 910 sends the exposure signal to the X-ray generation module 104. Thus, in these embodiments, the user always needs to go through the step of pressing down double gears (1004, 1005) before activating X-ray exposure. Particularly, in those embodiments, where the switch 1001 is a self-reset switch, the user may need to use two fingers, one pressing and holding the switch 1001 and the other pressing down the double gears (1004, 1005) to activate X-ray exposure.

In some embodiments, the exposure controller 910 functions as a supplement to software exposure controlling mechanism. In other embodiments, the exposure controller 910 functions independently without a software mechanism.

In various embodiments, the exposure controller 910 may send signals to the X-ray generation module 104 in a wired or wireless fashion. Particularly, for wired signal transmission, signal lines 1008 may be used to connect the exposure controller 910 and X-ray generation module 104. Particularly, shielded wires can be used to shield signal transmission from interferences. Alternatively, for wireless signal transmission, both the exposure controller 910 and the X-ray generation module 104 may include corresponding wireless transmission devices. Accordingly, in these embodiments, the exposure controller 910 may not include the signal line 1008.

In various embodiments described above, the X-ray generation module 104 may include a high-voltage generator (not shown in FIG. 10) and an X-ray tube (not shown in FIG. 10), when permission from both the switch 1001 and the double gear button (1004, 1005) are received, the high voltage generator permits the X-ray tube to generate and emit X-ray; otherwise the high voltage generator forbids the X-ray tube to generate or emit X-ray.

The switch 1001 may be various types, such as a micro-switch, stir switch, touch sense switch and other mechanical switch or soft switch. The protective groove 1007 and movable baffle 1003 may have various shapes, such as square, rectangular, round, oval, polygonal, or cambered, etc., according to particular needs in practice. The handle 1006 may have additional surface structures and/or textures according to particular need in practice, including but not limited to grooves, embossments, gripping, and/or other suitable structures or profiles, which may provide convenience and comfort for a user to hold the exposure controller 910 for a prolonged period.

The structures and functions described above in relation to the exposure controller 910 are not exhaustive and are not limiting; numerous other changes, substitutions, variations, alterations, and modifications may be ascertained to one skilled in the art and it is intended that the present disclosure encompasses all such changes, substitutions, variations, alterations, and modifications as falling within the scope of the appended claims.

In practice, communication between end users of the system may be performed before activating X-ray exposure. For instance, a doctor may require a patient to make and maintain in a particular body posture before image acquisition. Accordingly, in some embodiments, the exposure controller 910 further includes an audio device that enables communication between the end users. In addition to communication between end users, in some embodiments, the audio device 1101 may be configured to transit voice commands of an end user to the control module 103 of the system.

Particularly, integrating an audio device into the exposure controller 910 can have several advantageous. First, it can make the operation of the system more easy and convenient for an end user (such as a doctor). For example, when operating the exposure controller with both hands, a doctor can simply talk to the nearby audio device on the exposure controller 910, instead of approaching a faraway audio device, such as one on the console. Further, incorporating an audio device onto the exposure controller 910 may improve communication quality and safety of the system, as well as reduce cost of the system to some extent.

Figure 11:
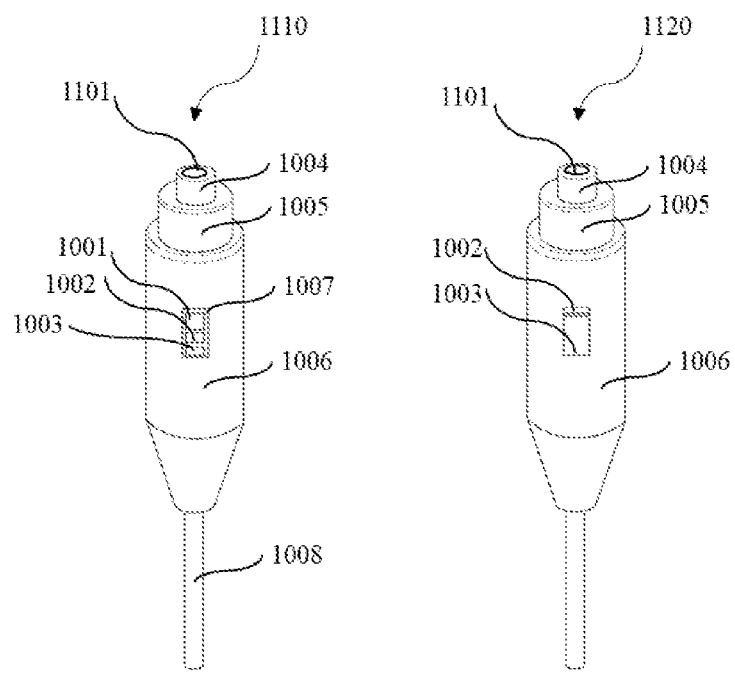
FIG. 11 illustrates an exemplary embodiment of an exposure controller according to the present disclosure.

FIG. 11 shows an exemplary embodiment of the exposure controller 910 where at least one audio device 1101 is installed near the first gear 1004 on one end of the handle 1006. In this particular embodiment, the audio device 1101 is embedded in a groove on the top of the first gear 1004. Yet, in other embodiments, the audio device 1101 may be placed at other positions of the exposure controller 910.

In various embodiments, the exposure controller 910 may send voice communication in a wired or wireless fashion. Particularly, for wired communication, signal lines 1008 may be used to connect the exposure controller 910 to the control module 103 and/or a loudspeaker (not shown) in the imaging room. Particularly, shielded wires can be used to shield communication from interferences. Alternatively, for wireless signal transmission, the exposure controller 910, the control module 103 and/or the loudspeaker may include corresponding wireless transmission devices. Accordingly, in these embodiments, the exposure controller 910 may not include the signal line 1008.

According to one aspect of the present disclosure, provided herein is a power supply system. The power supply system is configured to supply power through a high-voltage generator 1203, and thus can supply power to medical imaging devices including but not limited to the present digital radiography system.

Figure 12:
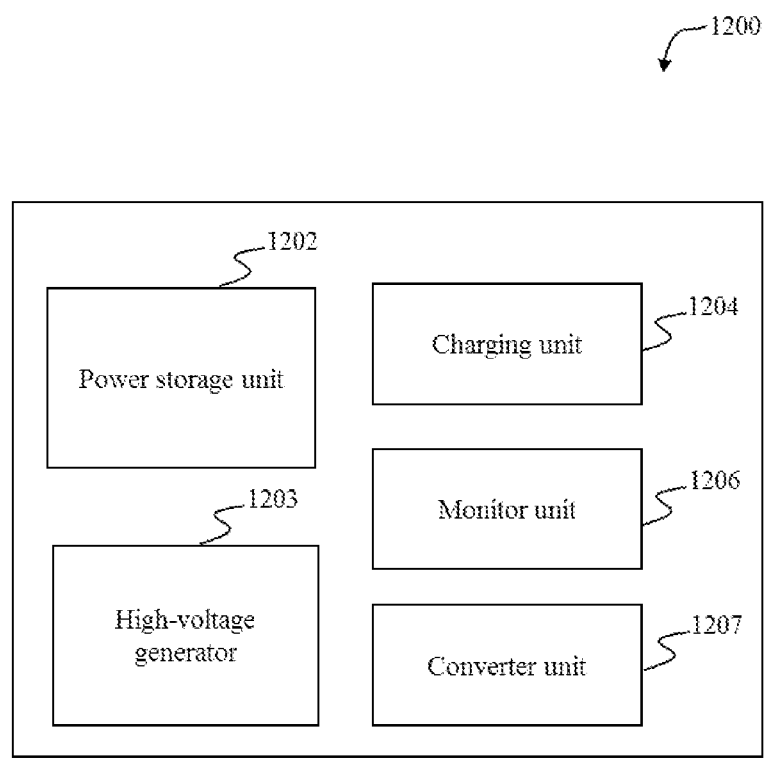
FIG. 12 is a block diagram illustrating an exemplary embodiment of a power supply system according to the present disclosure.

FIG. 12 is a block diagram illustrating an exemplary embodiment 1200 of the power supply system according to the present disclosure. As shown, the power supply system 1200 may include one or more power storage unit 1202, high-voltage generator 1203, charging unit 1204, monitor unit 1206, converter unit 1207 and/or any other suitable component. Power supply system 1200 may be used to supply power for medical imaging devices. For example, the power supply system 1200 can be one embodiment of the power supply module 101 that supplies power for the operation module 110 in FIG. 1. In some embodiments, power supply system 1200 may have the structures and functions as described in further details below in relation to FIGS. 13-17.

The power storage unit 1202 may be any kind of equipment that can store and supply power. In one embodiment, the power storage unit 120 may include a battery (such as a fuel cell, electrochemical cell, etc.), an energy-storage element (such as a capacitor, inductor, etc.), or the like, or a combination thereof. For example, the power storage unit 1202 may be the battery 1303 or capacitor 1304 as shown in FIGS. 13-17. In one embodiment, there may be one power storage unit 1202 in power supply system 1200. The power storage unit 1202 may connect to the high-voltage generator 1203. In another embodiment, there may be multiple power storage units 1202. For example, there may be two power storage units 1202 in the power supply system 1200. Particularly, a first power storage unit 1202 may be connected to the high-voltage generator 1203, and a second power storage unit 1202 may be connected to the first power storage unit 1202.

The high-voltage generator 1203 may be any kind of equipment that may generate a high electric voltage. For example, the high-voltage generator 1203 may be a direct current (DC) high-voltage generator, alternating current (AC) high-voltage generator, or the like, or a combination thereof. In one embodiment, the high-voltage generator 1203 may share one power storage unit 120 with other devices. For example, the high-voltage generator 1203, X-ray detector 415, motor driver 401-407, and motor 408-414 as shown in FIG. 4 may connect with the same power storage unit 120. In another embodiment, the high-voltage generator 1203 may have its own independent power storage unit 120. For example, the high-voltage generator 1203 may connect to a first power storage unit 120, and the X-ray detector 415, motor driver 401-407, and motor 408-414 as shown in FIG. 4 may connect to a second power storage unit 120.

The charging unit 1204 may be configured to charge a power storage unit 120 using a power supply. For example, the power supply may be from a power network, a battery or an energy-storage element, or the like, or a combination thereof. The charging method of the charging unit 1204 may be wire or wireless. For example, the charging unit 1204 may charge a power storage unit 120 using an electromagnetic field. In some embodiment, the charging unit 1204 may include some control circuits (not shown in FIG. 12). For example, the charging unit 1204 may charge a power storage unit 1202 with a current limit or voltage limit. In some embodiments, the charging unit 1204 may be in the form of a charge up circuit 1302, a voltage limiting charge up circuit 1602, and a current limiting charge up circuit 1502 as shown in FIGS. 13-17.

Figure 15:
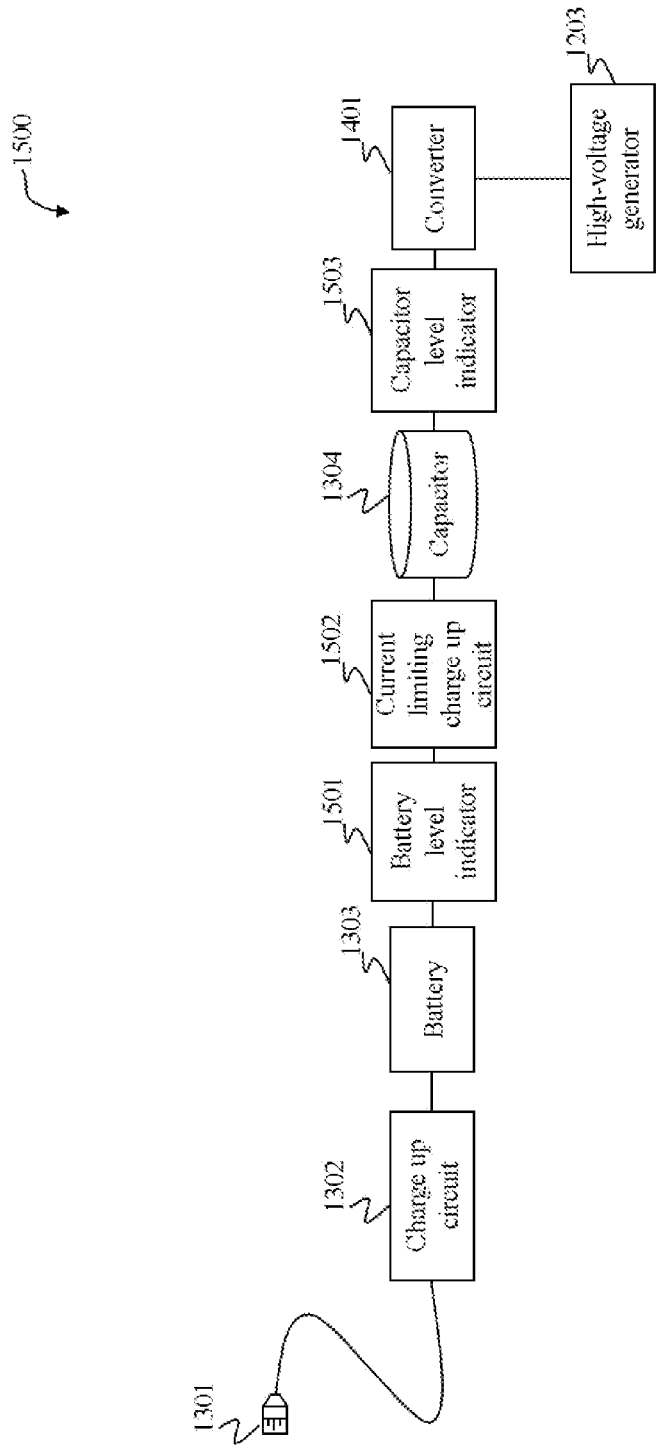
Figure 16:
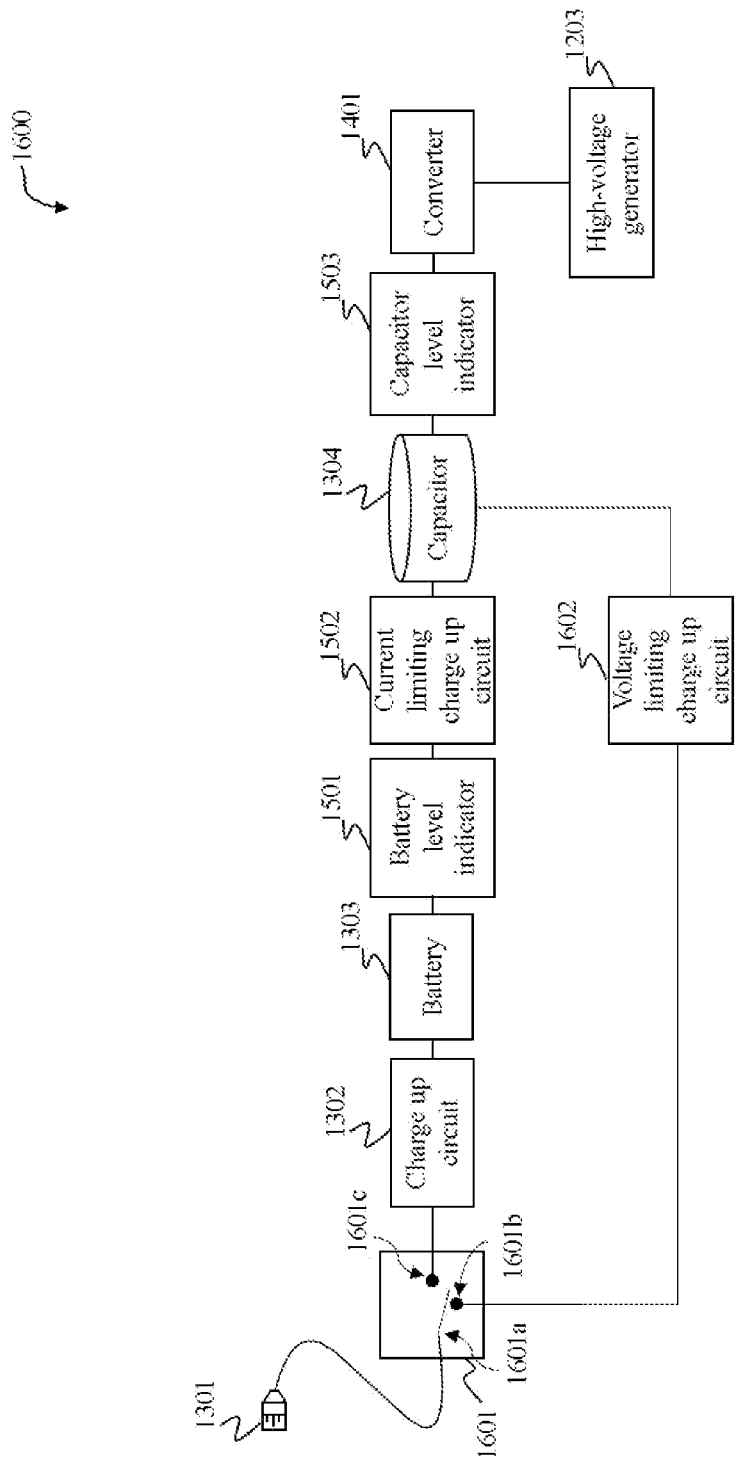
Figure 17:
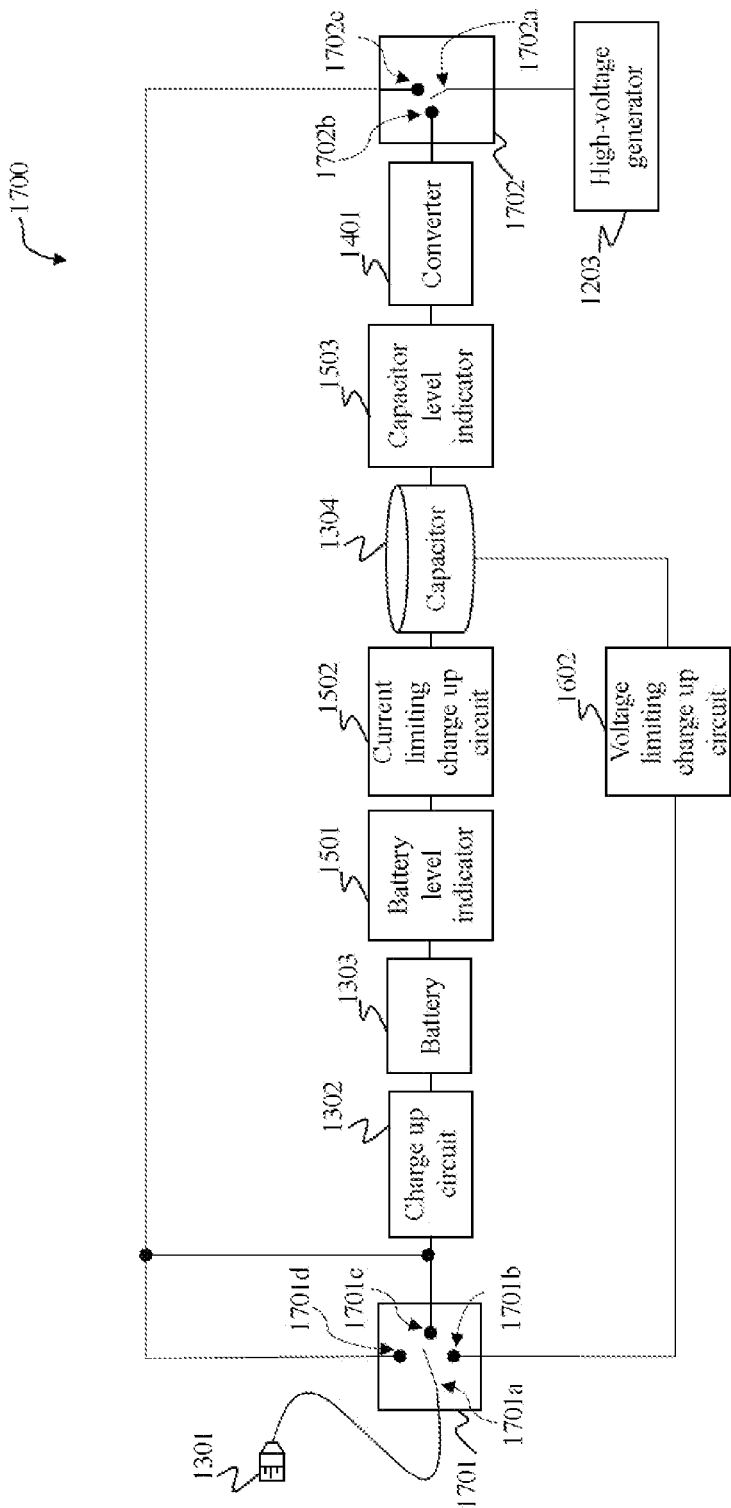

The monitor unit 1206 may be configured to monitor the power of the power storage unit 1202. For example, the monitor unit 1206 may be a battery level indicator 1501 or a capacitor level indicator 1503 as shown in FIGS. 15-17.

The converter unit 1207 may be configured to convert the electrical characteristics (such as voltage, current, frequency, power-phase, etc.) of the power storage unit 1202. In some embodiments, the converter unit 1207 may be a rectifier circuit (such as converting direct current to alternating current, converting one direct current to another direct current, etc.), a power inverter (such as converting direct current to alternating current), an AC frequency converter, a DC transformer, or the like, or a combination thereof. The converter unit 1207 may connect to the power storage unit 1202 and a power consumption equipment (e.g., high-voltage generator 1203.).

The structures and functions described above in relation to the power supply system 1200 are not exhaustive and are not limiting; numerous other changes, substitutions, variations, alterations, and modifications may be ascertained to one skilled in the art and it is intended that the present disclosure encompasses all such changes, substitutions, variations, alterations, and modifications as falling within the scope of the appended claims. For example, the power storage unit 1202 may be replaced by a power network.

Figure 13:
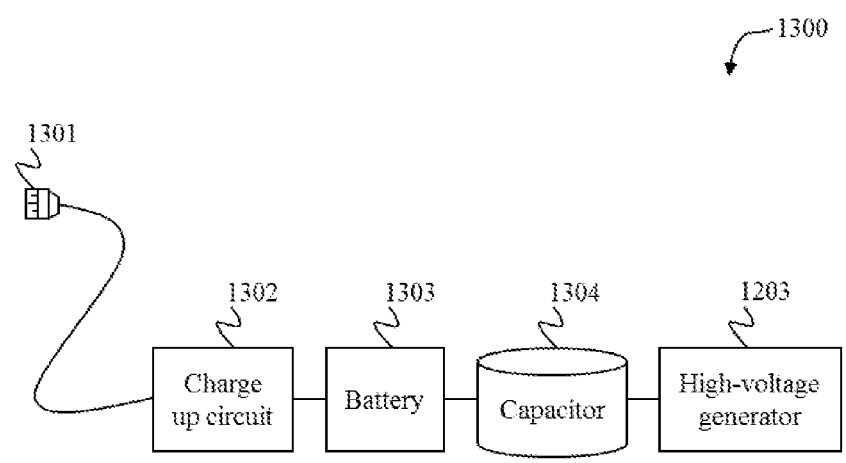
FIGS. 13 through 17 illustrate exemplary embodiments of a power supply system according to the present disclosure.

FIG. 13 illustrates an exemplary embodiment 1300 of the power supply system 1200 according to the present disclosure. As shown, the power supply system 1300 may include a power connector 1301, a charge up circuit 1302, a battery 1303, a capacitor 1304 and a high-voltage generator 1203. The power supply system 1300 may be configured for supplying power for medical imaging devices. For example, the power supply system 1300 may be one embodiment of the power supply module 101 that supplies power for the operation module 110 in FIG. 1. The power supply system 1300 may be moveable or non-moveable.

The power connector 1301 may be configured for connecting the charge up circuit 1302 with a power supply. In some embodiments, the power connector 1301 may be a one-pin plug, two-pin plug, three-pin plug, four-pin plug, or the like, or a combination thereof. For example, the power connector 1301 may be a UL-NEMA 5-15 USA 3 pin plug to connect an outlet socket of a power network. In another example, the power connector may be a 2-pin plug without the earth pin.

The charge up circuit 1302 may be configured to charge a battery 1303 with a power supply through the power connector 1301. In some embodiments, the charge up circuit 1302 may correspond to or be part of the charging unit 1204 as in FIG. 12. In some embodiments, the charge up circuit 1302 may have an overcharge protection sub-unit. The overcharge protection sub-unit may be configured to prevent overcharge damage to the battery 1303. For example, the overcharge protection sub-unit may sense overcharging and disrupt the connection between the battery 1303 and the charge up circuit 1302.

The battery 1303 and capacitor 1304 may be configured to store and supply power. In some embodiments, the battery 1303 and the capacitor 1304 may correspond to or be part of the power storage unit 1202 in FIG. 12.

Referring to FIG. 13, the battery 1303 may connect to the capacitor 1304 and the charge up circuit 1302. For example, the battery may be a lithium cell, nickel-cadmium cell, or the like, or a combination thereof. The battery 1303 may supply power to the capacitor 1304 and the operation module 110 in FIG. 1. In some embodiments, the battery 1303 may supply power to the capacitor 1304, which in turn may supply power to the high-voltage generator 1203. As such, large current discharge from the battery 1303 is avoided for activating the high-voltage generator 1203, and the battery lifetime may be improved.

The capacitor 1304 may connect to the battery 1303 and the high-voltage generator 1203. Referring to FIG. 13, the capacitor 1304 may receive power form the battery 1303 and supply power to the high-voltage generator 1203. In some embodiments, the capacitor 1304 may be a ceramic capacitor, a dacron capacitor, a electrolytic capacitor, or the like, or a combination thereof. For example, the capacitor 1304 may be a supercapacitor. In some embodiments, the capacitor 1304 may be a green energy source without polluting the environment. In some embodiments, the capacitor 1304 may have a longer cycle life. For example, the capacitor 1304 may have more than 1 million charge-discharge cycles. In some embodiments, the capacitor 1304 may have a rapid charging and discharging speed. For example, the charging or discharging time of the capacitor 1304 may be between 0.3 s~15 mins. In another example, the charging or discharging time of the capacitor 1304 may be shorter than 0.01 s. In some embodiments, the capacitor 1304 may have a high charge-discharge efficiency. For example, the charge-discharge efficiency of the capacitor 1304 may be above 70%. In another example, the charge-discharge efficiency of the capacitor 1304 may be above 90%.

The structures and functions described above in relation to the power supply system are not exhaustive and are not limiting; numerous other changes, substitutions, variations, alterations, and modifications may be ascertained to one skilled in the art and it is intended that the present disclosure encompasses all such changes, substitutions, variations, alterations, and modifications as falling within the scope of the appended claims. For example, there may be a converter circuit between the capacitor 1304 and the high-voltage generator 1203.

Figure 14:
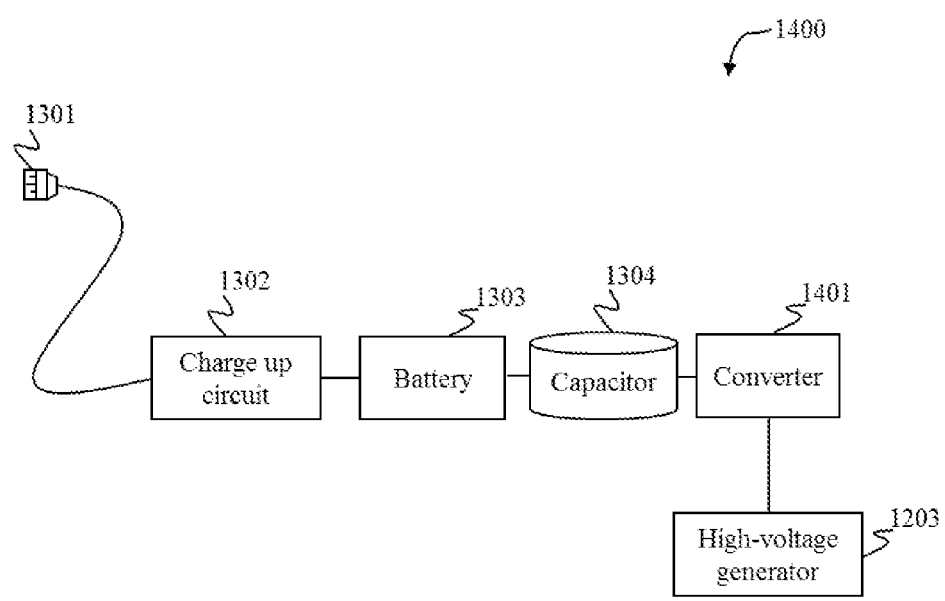

FIG. 14 illustrates another exemplary embodiment 1400 of the power supply system 1200 according to the present disclosure. As shown, the power supply system 1400 may include a power connector 1301, a charge up circuit 1302, a battery 1303, a capacitor 1304, a converter 1401 and a high-voltage generator 1203.

The converter 1401 may be configured to convert the electrical characteristics (e.g., voltage, current, frequency, power-phase, etc.) of the capacitor 1304. In some embodiments, the converter 1401 may correspond to or be part of the converter unit 1207 in FIG. 12. In one embodiment, the high-voltage generator 1203 may be an AC high-voltage generator without a DC/AC converting function, thus the converter 1401 is needed to convert DC output of the capacitor 1304 into AC for the AC high-voltage generator. In another embodiment, the high-voltage generator 1203 may need an input voltage out of the output range of the capacitor 1304, thus the converter 1401 is needed to modify the voltage for the high-voltage generator 1203.

The structures and functions described above in relation to the power supply system are not exhaustive and are not limiting; numerous other changes, substitutions, variations, alterations, and modifications may be ascertained to one skilled in the art and it is intended that the present disclosure encompasses all such changes, substitutions, variations, alterations, and modifications as falling within the scope of the appended claims.

FIG. 15 illustrates another exemplary embodiment 1500 of the power supply system 1200 according to the present disclosure. As shown, the power supply system 1500 may include a power connector 1301, a charge up circuit 1302, a battery 1303, a battery level indicator 1501, a current limiting charge up circuit 1502, a capacitor 1304, a capacitor level indicator 1503, a converter 1401 and a high-voltage generator 1203.

The battery level indicator 1501 may be configured to monitor the power level of the battery 1303. In some embodiments, the battery level indicator 1501 may correspond to or be part of the monitor unit 1206 in FIG. 12. In some embodiments, the battery level indicator 1501 may include a detection sub-unit and a switch (no shown in FIG. 15). The detection sub-unit may be configured to detect the amount of fuel left in the battery 1303. For example, the detection sub-unit may be an electric quantity measurement chip, a semiconductor component, a circuit, or the like, or a combination thereof. If the amount of fuel left is lower than a threshold, the battery indicator 1501 may stop the battery 1303 from supplying power to the capacitor 1304. For example, the threshold may be a ratio (such as 10%, 20%, 30%, etc.) or a value (such as 100 A·H, 200 A·H, 300 A·H, etc.), or the like, or a combination thereof. The battery indictor 1501 may stop power supply from the battery 1303 to the capacitor 1304 by disconnecting the switch. In some embodiments, the battery level indicator 1501 may include a display sub-unit (no shown in FIG. 15). The display sub-unit may be configured to display the amount of fuel left in the battery 1303. For example, the display sub-unit may be a liquid crystal displayer, a LED, or the like, or a combination thereof. The use of battery level indicator 1501 may avoid undesired deep discharge of the battery 1303.

The current limiting charge up circuit 1502 may be configured to charge the capacitor 1304 with a current limit. The use of the current limiting charge up circuit 1502 may avoid undesired large-current discharge of the battery 1303. In some embodiments, the current limiting charge up circuit 1502 may correspond to or be part of the charging unit 1204 in FIG. 12.

The capacitor level indicator 1503 may be configured to monitor the power level of the capacitor 1304. In some embodiments, the capacitor level indicator 1503 may correspond to or be part of the monitor unit 1206 in FIG. 12. In some embodiments, the capacitor level indicator 1503 may include a calculation sub-unit, an execution sub-unit, a display sub-unit (not shown in FIG. 15), or the like, or a combination thereof. The calculation sub-unit may be configured to calculate how many times the high-voltage generator 1203 can still be activated with the power remaining in the capacitor 1304. The execution sub-unit may be configured to prevent the capacitor 1304 from supplying power to the high-voltage generator 1203 under certain conditions, such as when the calculated number is below a threshold (such as 3, 2, 1, etc.). The display sub-unit may be configured to display the calculated number. For example, the display sub-unit may be a liquid crystal displayer, a LED, or the like, or a combination thereof.

The structures and functions described above in relation to the power supply system are not exhaustive and are not limiting; numerous other changes, substitutions, variations, alterations, and modifications may be ascertained to one skilled in the art and it is intended that the present disclosure encompasses all such changes, substitutions, variations, alterations, and modifications as falling within the scope of the appended claims. For example, the battery level indicator 1501 and the capacitor level indicator 1503 may share a same display sub-unit.

FIG. 16 illustrates another exemplary embodiment 1600 of the power supply system 1200 according to some embodiments of the present disclosure. As shown, the power supply system 1600 may include a power connector 1301, a selection sub-unit 1601, a charge up circuit 1302, a battery 1303, a battery level indicator 1501, a current limiting charge up circuit 1502, a capacitor 1304, a capacitor level indicator 1503, a converter 1401, a high-voltage generator 1203 and a voltage limiting charge up circuit 1602.

The selection sub-unit 1601 is configured to form at least two different circuits for the power supply based on selection. Particularly, as shown in FIG. 16, the selection sub-unit 1601 may include an input node 1601a, a first output node 1601b and a second output node 1601c. The input node 1601a may connect with the first output node 1601b to form a first circuit for power supply, or may connect with the second output node 1601c to form a second circuit for power supply. In some embodiments, the selection sub-unit 1601 may be a selection circuit, a multi-way switch, a multiplexer, or the like, or a combination thereof. In this embodiment, when the input node 1601a connects to the first output node 1601b, a power network may charge the capacitor 1304 through the voltage limiting charge up circuit 1602; when the input node 1601a connects to the second output node 1601c, the battery 1303 may charge the capacitor 1304. Particularly, the first circuit may be selected when the battery 1303 in the second circuit cannot supply power to the capacitor 1304, such as the battery power is too low.

When the first circuit is selected, the voltage limiting charge up circuit 1602 may charge the capacitor 1304 with a voltage limit. With using the voltage limiting charge up circuit 1602, the capacitor 1304 may receive power supply from a power network. In some embodiments, the voltage limiting charge up circuit 1602 may correspond to or be part of the charging unit 1204 in FIG. 12.

The structures and functions described above in relation to the power supply system are not exhaustive and are not limiting; numerous other changes, substitutions, variations, alterations, and modifications may be ascertained to one skilled in the art and it is intended that the present disclosure encompasses all such changes, substitutions, variations, alterations, and modifications as falling within the scope of the appended claims.

FIG. 17 illustrates another exemplary embodiment 1700 of the power supply system 1200 according to the present disclosure. As shown, the power supply system 1700 may include a power connector 1301, a first selection sub-unit 1701, a second selection sub-unit 1702, a charge up circuit 1302, a battery 1303, a battery level indicator 1501, a current limiting charge up circuit 1502, a capacitor 1304, a capacitor level indicator 1503, a converter 1401, a high-voltage generator 1203 and a voltage limiting charge up circuit 1602.

The first selection sub-unit 1701 may include an input node 1701a, a first output node 1701b, a second output node 1701c, and a third output node 1701d. The first selection sub-unit 1701 may be configured to select an output node among the three output nodes (1701b, 1701c, 1701d) form a power supply circuit. The position of the first selection sub-unit 1701 in the circuit may be between the battery 1303 and the power connector 1301. For example, as shown in FIG. 17, the first selection sub-unit 1701 may connect to the charge up circuit 1302 and the power connector 1301.

The second selection sub-unit 1702 may include an output node 1702a, a first input node 1702b, and a second input node 1702c. The second selection sub-unit 1702 may be configured to select an input node between the first input node 1702b and the second input node 1702c to form a power supply circuit. Position of the second selection sub-unit 1702 in the circuit may be between the capacitor 1304 and the high-voltage generator 1203. For example, as shown in FIG. 17, the second selection sub-unit 1702 may connect to the converter 1401 and the high-voltage generator 1203.

In some embodiments, the first selection sub-unit 1701 and the second selection sub-unit 1702 may be a selection circuit, a multi-way switch, a multiplexer, or the like, or a combination thereof.

As shown in FIG. 17, multiple power supply circuits may be formed depending on the selections at the first selection sub-unit 1701 and the second selection sub-unit 1702. Particularly, a third circuit is formed when input node 1701a connects to output node 1701c, and the input node 1702b connects to output node 1702a. In this power supply circuit, the power network may charge the battery 1303 through the charge up circuit 1302. The battery 1303 may charge the capacitor 1304. The capacitor 1304 may supply power to the high-voltage generator 1203. In some embodiments, when the battery level reaches a preset threshold, connection between the power network and the battery 1303 may be discontinued.

A fourth circuit is formed when input node 1701a connects to output node 1701b, and input node 1702b connects to output node 1702a. In this power supply circuit, the power network may charge the capacitor 1304 through the voltage limiting charge up circuit 1602. The capacitor 1304 may charge the high-voltage generator 1203. This power supply circuit may be selected when there is a need to fast charge the capacitor 1304.

A fifth circuit is formed when input node 1701a connects to output node 1701d, and input node 1702c connects to the output node 1702a. In this power supply circuit, the power network may supply power to the high-voltage generator 1203, while at the same time the power network may charge the battery 1303, and the battery 1303 may charge the capacitor 1304. In some embodiments, the battery 1303 may simultaneously receive power from the power network and supply power to the capacitor 1304 and/or the operation module 110 of the digital radiography system (see e.g., FIG. 1).

Figure 18:
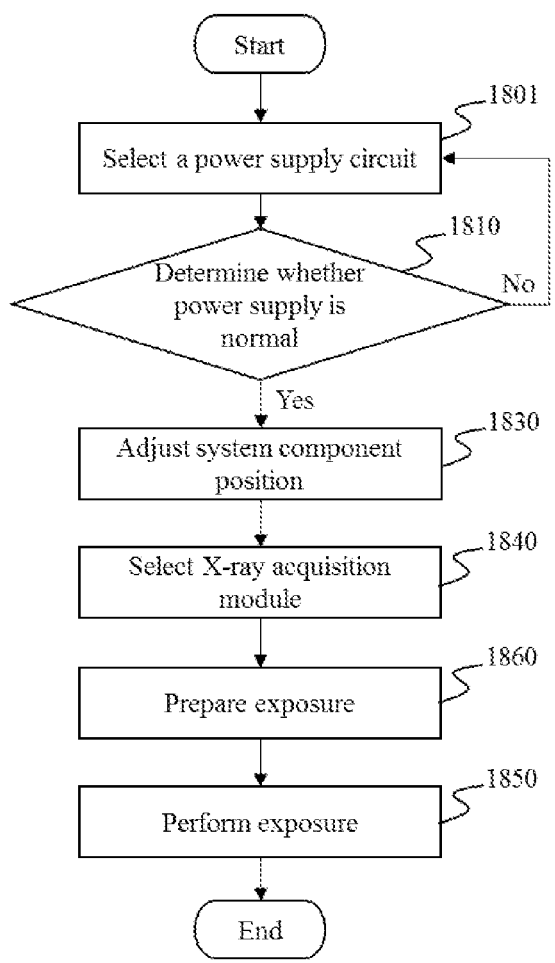
FIG. 18 is a flowchart illustrating an exemplary process of the digital radiography system according to some embodiments of the present disclosure.

FIG. 18 is a flowchart showing an exemplary process of the digital radiography system according to some embodiments of the present disclosure. In step 1801, a power supply circuit may be selected. The power circuit may be any circuit according to FIGS. 13-17 and related descriptions. In step 1810, a determination as to whether the power supply is normal may be performed. The determination may be performed by the system, or may be performed by any module of the system, or may be performed by a power detection device independent to the system (not shown), or may be performed by a power detection unit (not shown) integrated in any module of the system, or may be performed by a peripheral equipment (not shown) related to the system. The determination may be performed based on a pre-set rule. The pre-set rule may be a specific value, or may be a value range, or may be a current/voltage status. For example, if the quantity of the power supply is less than a pre-set threshold value, an alarm signal representing low power may be generated. Based on the alarm signal, in some embodiments, a charging operation may be performed by the power supply module 101. In some embodiment, an external power supply (e.g., a battery, a charging device, etc.) may be provided. In some embodiments, the system may be controlled to enter to a sleeping mode or a standby mode.

If the power supply is normal through step 1810, or if the quantity of the power supply reaches the pre-set threshold value, a system component's position may be adjusted in step 1830. The component may be any component of the system, including but not limited to the X-ray detector 230, the ceiling suspension unit 240, the tube stand 250, the X-ray tube 260, the beam limiting device 270, or the like. The adjusting may be performed by the control module 103, or may be performed by the control unit (not shown) integrated in the control module 103. The adjusting may include adjusting the motion speed, adjusting the motion route, tilting an angle, or the like, or a combination thereof. More detailed descriptions regarding the controlling or adjusting of the motion of the system components may be found in FIGS. 3-4 and other related descriptions.

After the positions of system components are adjusted and determined, an X-ray acquisition module 106 of a specific configuration may be selected in step 1840. The selection of the X-ray acquisition module 106 of the specific configuration may be performed by the control module 103, or may be performed by a selection unit (not shown) integrated in the control module 103, or may be performed by a selection unit (not shown) integrated in the X-ray acquisition module 106. The specific configuration may be a vertical configuration, a horizontal configuration, a free-style configuration, or the like.

After the X-ray acquisition module 106 is selected, step 1860 for preparing exposure may be performed. The preparation may include setting one or more exposure parameters, including but not limited to exposure duration (ED), exposure frequency (EF), adherence factor (AF), body weight (BW), event frequency (EV), intake rate (IR), surface area of exposed skin (SA), age dependent adjustment factor (ADAF), or the like, or a combination thereof. The exposure parameters may be prepared based on a feature of the imaging target, or may be set by the system default. After the exposure parameters are set, an exposure for obtaining an X-ray image may be performed in step 1850.

The structures and functions described above in relation to the system process are not exhaustive and are not limiting; numerous other changes, substitutions, variations, alterations, and modifications may be ascertained to one skilled in the art and it is intended that the present disclosure encompasses all such changes, substitutions, variations, alterations, and modifications as falling within the scope of the appended claims. For example, in order to guarantee a normal operation of the system, a power detection step (such as step 1810) may be performed between any two steps. In another example, after selecting an X-ray acquisition module of a specific configuration in step 1840, a step for adjusting positions of system components (such as step 1803 may be performed).

Figure 19:
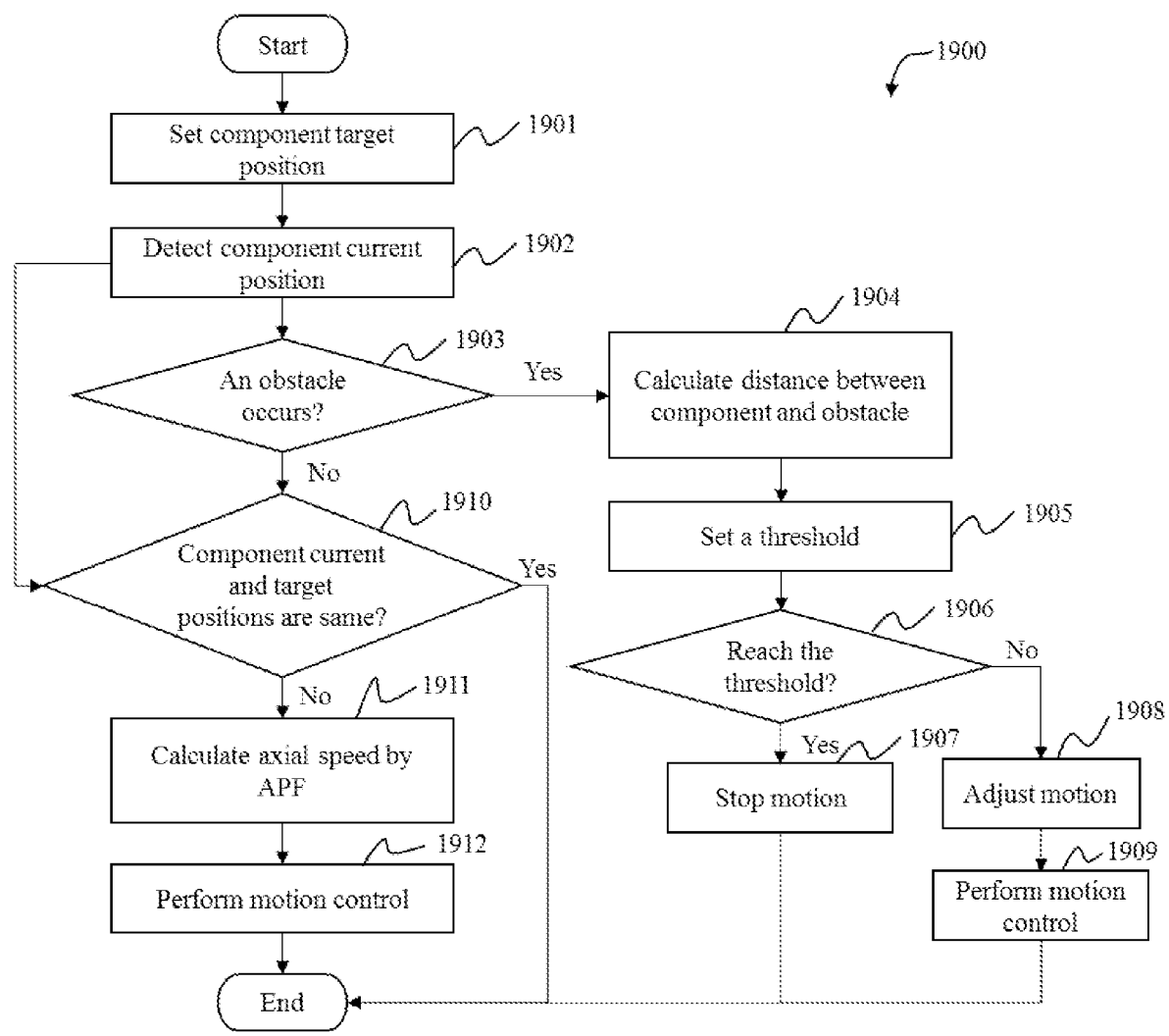
FIG. 19 illustrates an exemplary process for adjusting and determining positions of system components according to some embodiments of the present disclosure.
Figure 20:
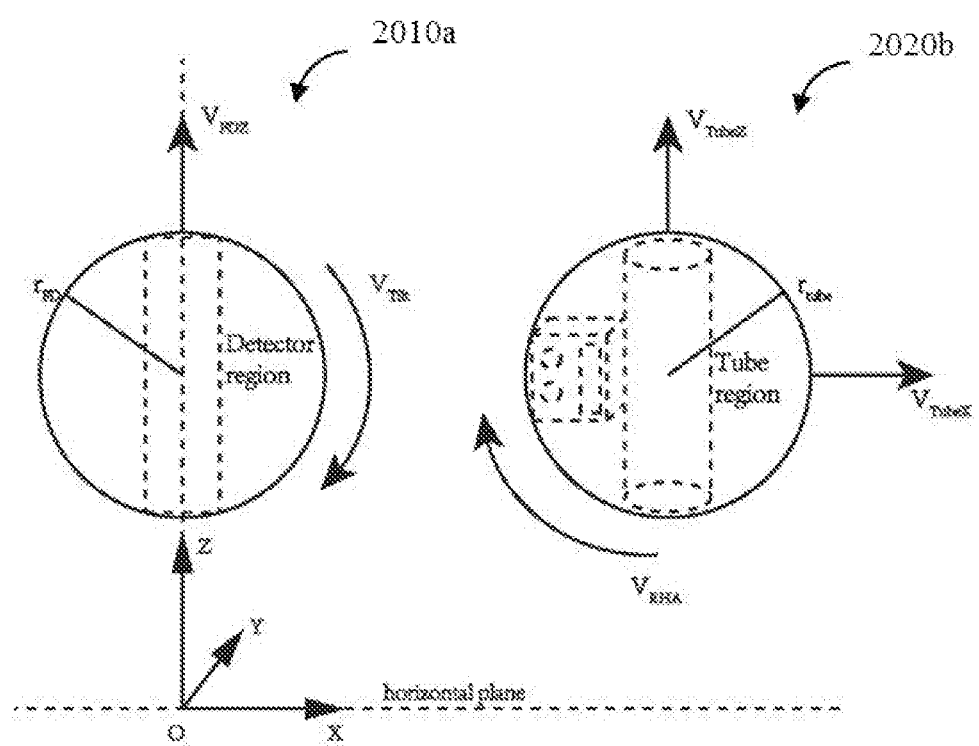
FIG. 20 illustrates an exemplary method for determining an collision area according to the APF method.

The step for adjusting positions of system components (such as step 1803) according several embodiments is disclosed in further details in relation to FIGS. 19 through 21. FIG. 19 provides an exemplary process for adjusting and determining positions of system components according to some embodiments of the present disclosure. The adjusting may be performed in order to avoid accidental collision, and/or to ensure optimum position and angle of the components for imaging. A target position of a system component may be set in step 1901. The target position may be set by the system default, or by a medical practitioner (e.g., a doctor) or other end users. A current position of the component may be detected in step 1902. The detection may be performed by way of a sensing method, or may be performed by way of a mathematical calculation method. Then the system may detect whether an obstacle occur in step 1903. The detection may be performed by a sensing method (e.g., using a proximity sensor placed on the component). If the answer is "Yes," the process may proceed to step 1904 to calculate a distance between the component and the obstacle. The calculation may be performed by the control module 103, or may be performed by a calculation unit (not shown) integrated in the component, or may be performed by the processing module 105, or may be performed by any processing device that may be used as a calculation device disclosed anywhere in the present disclosure. A threshold for the distance may be set in step 1905. The threshold may be set by the system default, or by a medical practitioner (e.g., a doctor) or other end users. The threshold may be a single value, or may be a value range.

In step 1906, a comparison between the calculated distance and the preset threshold may be performed. If the distance reaches or exceeds the threshold, the motion of the component may be stopped in step 1907. If the distance is within the threshold range, the motion of the component may be adjusted in step 1908. For example, the motion speed of the component may be reduced. In another example, the component may be tilted for a specific angle to avoid collision. In a further example, the component may be turned around to another direction. After the motion of the component is adjusted, a motion control may be performed in step 1909. The motion control may be performed by the control module 103, or may be performed by a peripheral equipment (not shown) related to the system, or may be performed by any processing device disclosed anywhere in the present disclosure. The motion control may be continuous in real time, or may be performed at certain time intervals.

If no obstacle is detected in step 1903, the process may proceed to step 1910 to determine whether the current position and the target position are the same. If the answer is "Yes," no motion is needed. If the answer is "No", axial speeds may be calculated based on potential field method in step 1911 (such as artificial potential field (APF)). The calculation process of the potential field method will be described in further details below in relations to FIGS. 20-21. Then a motion control may be performed in step 1912. Similarly, the motion control may be performed by the control module 103, or may be performed by a peripheral equipment (not shown) related to the system, or may be performed by any processing device disclosed anywhere in the present disclosure.

As described above in the present disclosure, the motion path of system components may be calculated using the artificial potential field (APF) method. Particularly, APF is a mathematical approach for path planning as an object moves towards a target position, which assumes that the target position generates attractive forces towards the object, while nearby obstacles generates repulsive forces against the object. By calculating net forces of the repulsive and attractive forces, the object's motion path may be calculated. Regarding the structure of the present digital radiography system, any moving system component may be considered as the object in APF. It should be noted that when calculating the motion path of one system component, that system component may be regarded as the object to be moved to a target position, while another system component may be considered as an obstacle in APF. Similarly, objects external to the system, such as an imaging target or furniture in the imaging room, may be considered as obstacles in APF. For example, when calculating the motion path of the X-ray tube, the repulsive force generated by the X-ray detector may be calculated. Below provided are exemplary calculations based on two components of the present system, namely the X-ray tube and the X-ray detector.

Particularly, FIG. 20 illustrates an exemplary path planning for the X-ray tube and X-ray detector of the present system using the APF method. As shown in the figure, the collision area of an X-ray tube is denoted as the tube region in right panel 2020b, which is a sphere of radius $r_{Tube}$. Likewise, the collision area of the X-ray detector is denoted as the detector region in left panel 2010a, which is a sphere of radius $r_{FD}$. The axial speed in the X axis and Z axis of the tube are denoted by $V_{TubeX}$ and $V_{TubeZ}$, respectively. The axial speed in Z axis of the detector is denoted as $V_{FDZ}$. The rotation speed of the tube and the detector are $V_{RHA}$ and $V_{Tilt}$, respectively. As a result, the collision area of the tube and the detector may not be influenced by the corresponding rotation speed $V_{RHA}$ and $V_{Tilt}$. The rotation speed $V_{RHA}$ and the rotation speed $V_{Tilt}$ may be calculated based on proportional integral derivative (PID) by the following equations:

$$V_{RHA}=K_{Rp}(\Delta P_{Rt}+1/T_{Ri}\Sigma \Delta P_{Rt}\Delta t+T_{Rd}(\Delta P_{Rt}-\Delta P_{Rt-1})/\Delta t)$$

$$V_{Tilt}=K_{Tp}(\Delta P_{Tt}+1/T_{Ti}\Sigma \Delta P_{Tt}\Delta t+T_{Td}(\Delta P_{Tt}-\Delta P_{Tt-1})/\Delta t) \quad \text{(Equation 1)}$$

Where, $K_{Tp}$, $T_{Ti}$, $T_{Td}$, $K_{Rp}$, $T_{Ri}$, $T_{Rd}$ are PID constants that can be obtained by testing. $\Delta P_{Tt}$ is the difference of the target angle in Tilt axis and the angle at t moment, while $\Delta P_{Rt}$ is the difference of the target angle in TRHA axis and the angle at t moment, $\Delta t$ is sampling period.

Axial speeds $V_{FDZ}$, $V_{TubeX}$ and $V_{TubeZ}$ may determine the position of the collision area. To avoid collisions, axial speeds $V_{FDZ}$, $V_{TubeX}$ and $V_{TubeZ}$ may be influenced by the collision area. In some embodiments of the present disclosure, APF may be utilized to calculate the axial speeds of the tube and the detector, and the axial speeds may be updated constantly to accomplish obstacle avoidance and path planning.

FIG. 21-A is a flowchart illustrating exemplary path planning and FIG. 21-B is a diagram illustrating exemplary path planning for the X-ray tube and X-ray detector according to some embodiments of the present disclosure.

Particularly, when calculating the motion path of the tube, in step 2101, the repulsive force generated by the detector may be calculated.

If $D_{FT} \leq D_{max}$, the repulsive force may be calculated by:

$$\vec{F}_{FTX}=K_F \vec{D}_{FTX}/D_{FT}^2$$

$$\vec{F}_{FTZ}=K_F \vec{D}_{FTZ}/D_{FT}^2 \quad \text{(equation 2)}$$

Where $D_{FT}$ denotes the distance between the tube and the detector. Referring to FIG. 20, $D_{FT}$ equals to the distance of the rotation center of the tube and the rotation center of the detector minus $r_{FD}$ and $r_{Tube}$. $\vec{D}_{FTX}$ and $\vec{D}_{FTZ}$ are X component and Z component of $D_{FT}$ respectively. $D_{max}$ is a threshold distance where an obstacle starts to exert repulsive forces. $\vec{F}_{FTX}$ and $\vec{F}_{FTZ}$ are X component and Z component of the repulsive force generated by the detector, respectively. $K_F$ is a proportionality coefficient.

It should be noted that both repulsive forces and attractive forces in APF are artificially abstracted forces. For persons of ordinary skills in the art, it should be understood that the X component and the Z component of the repulsive force may be generated by the detector, while the X component and the Z component of the attractive force may be generated by the target position.

If $D_{FT} \geq D_{max}$, both $\vec{F}_{FTX}$ and $\vec{F}_{FTZ}$ may be set to 0. It may be inferred from equation 2 that the repulsive force generated by the detector increases as $D_{FT}$ decreases, when $D_{FT}$ approaches 0, the repulsive force generated by the detector may tend to be infinite, which may avoid the collision of the tube and the detector.

In step 2102, the attractive force generated by the target position may be calculated.

When $D_g \geq D_{min}$, the attractive force generated by the target position may be calculated by:

$$D_g = \begin{cases} D_{goal}(D_{goal} \geq D_{run}) \\ D_{run}(D_{goal} \leq D_{run}) \end{cases} \quad \text{(equation 3)}$$

$$\vec{F}_{goalX} = K_g \vec{D}_{goalX} D_g / D_{goal} \quad \text{(equation 4)}$$

$$\vec{F}_{goalZ} = K_g \vec{D}_{goalZ} D_g / D_{goal}$$

Where $\vec{F}_{goalX}$ and $\vec{F}_{goalZ}$ are X component and Z component of the attractive force generated by the target position, respectively. Kg is a proportionality coefficient. $D_{min}$ is a threshold distance between the target position and the current position of the moving component. $D_{goal}$ is a distance between the target position and the current position of the moving component. $D_{run}$ is a minimum threshold for the attractive force; $\vec{D}_{goalX}$ and $\vec{D}_{goalZ}$ are X component and Z component of $D_{goal}$ respectively.

When $D_{goal} < D_{min}$, it may be determined that the tube has arrived the target position, thus $\vec{F}_{goalX}$ and $\vec{F}_{goalZ}$ may be set to 0, and the calculation of the attractive force generated by the target position may be terminated. It should be noted that $D_{min}$ may be determined by accuracy requirement. $D_{run}$ may be set for an avoidance of slow movement of the object when the attractive force is not large enough.

In step 2103, the net force of the repulsive force and the attractive force may be calculated. Taking the movement of the tube as an example, the net force may be calculated by:

$$\begin{cases} \vec{F}_x = \vec{F}_{goalX} - \vec{F}_{FTX} \\ \vec{F}_z = \vec{F}_{goalZ} - \vec{F}_{FTZ} \end{cases} \quad \text{(equation 5)}$$

Where $\vec{F}_x$ is the net force in X axis and $\vec{F}_z$ is the net force in Z axis.

In step 2104, axial speeds of the tube may be calculated based on the net force calculated in step 2103. Taking the movement of the tube as an example, the axial velocities may be calculate by:

$$\vec{V}_x = \begin{cases} K_v \vec{F}_x |K_v \vec{F}_x| \leq |\vec{V}_{maxX}| \\ \vec{V}_{maxX} |K_v \vec{F}_x| > |\vec{V}_{maxX}| \end{cases} \quad \text{(equation 6)}$$

$$\vec{V}_z = \begin{cases} K_v \vec{F}_z |K_v \vec{F}_z| \leq |\vec{V}_{maxZ}| \\ \vec{V}_{maxZ} |K_v \vec{F}_z| > |\vec{V}_{maxZ}| \end{cases} \quad \text{(equation 7)}$$

Where $\vec{V}_x$ and $\vec{V}_z$ are X axial speed and Z axial speed, respectively, $K_v$ is transformation proportionality coefficient of forces and velocities, $\vec{V}_{maxX}$ and $\vec{V}_{maxX}$ are the maximum velocity in X axis and Z axis respectively.

It should be understood by persons of ordinary skill in the art that the axial speeds of the X-ray detector may be calculated based on the method described above. Particularly, to calculate the axial speeds of the detector, the X-ray tube may be regarded as an obstacle.

It should be noted that the flowchart described above is merely provided for the purposes of illustration, and not intended to limit the scope of the present disclosure. For persons of ordinary skills in the art, various variations and modifications may be conceptualized and reduced to practice. Those variations and modifications are intended to be within the scope of the present disclosure.

According to one aspect of the present disclosure, provided herein are methods for selecting an X-ray acquisition module of a suitable configuration. In practice, because X-ray images obtained from an imaging target in different positions may be desirable (for example, a doctor may need X-ray images of a patient when the patient stands up and lies down), a digital radiography system may include more than one X-ray acquisition modules. Particularly, the more than one X-ray acquisition modules may have a horizontal configuration (e.g., suitable for imaging a target in horizontal position) and a vertical configuration (e.g., suitable for imaging a target in vertical position). However, if the selection of a suitable X-ray acquisition module is performed manually by a medical practitioner (e.g., a doctor), error could happen when X-ray exposure occurs when an imaging target (e.g., a patient) is not in a suitable position relative to the selected X-ray acquisition module. Thus, provided herein is a method for automatically selecting an X-ray acquisition module of a suitable configuration, thereby increasing efficiency and safety of the digital radiography system.

Figure 22:
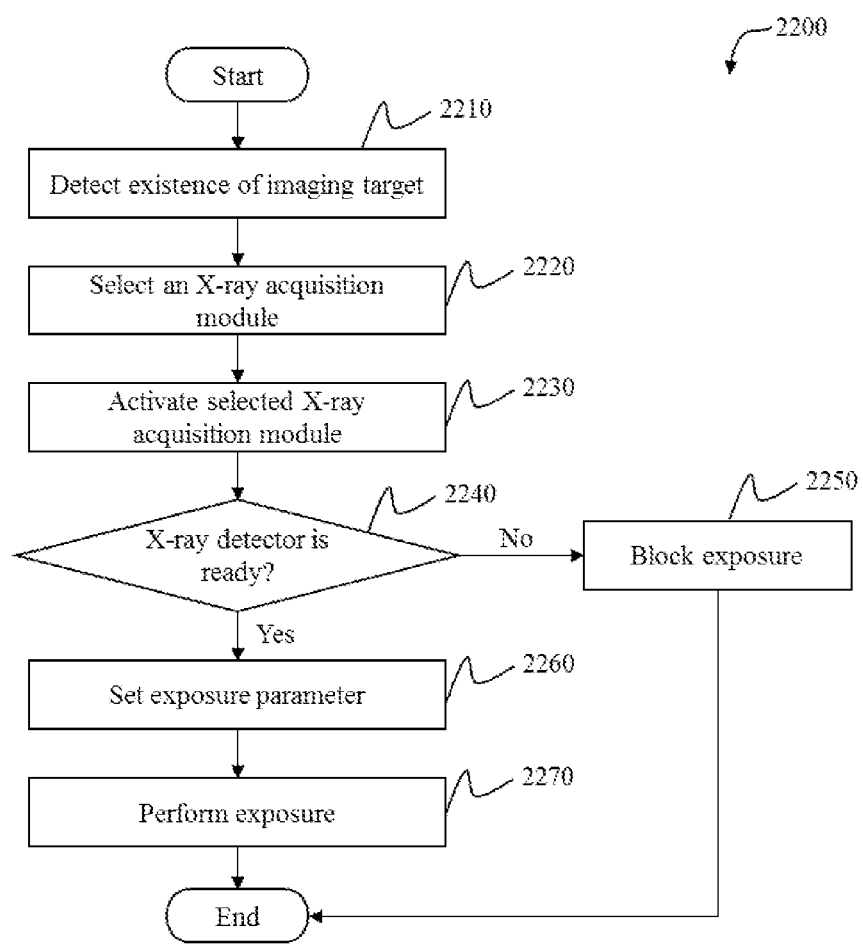
FIG. 22 illustrates an exemplary process of the digital radiography system according to some embodiments of the present disclosure.

FIG. 22 provides an exemplary process for selecting an X-ray acquisition module 106 according to some embodiments of the present disclosure. In step 2210, the system may detect whether an imaging target is in a suitable position relative to an X-ray acquisition module. Referring to FIG. 2-A, the detection may be performed by the first detection unit 2203, or may be performed by the second detection unit 2205, or may be performed by an external detection device (not shown) related to the system. In some embodiments, the detection may be performed by way of a sensing method, such as using an infrared sensing method. In some embodiments, the detection may be performed by way of a portrait discrimination method. In some embodiments, the detection may be performed using a radar technology. An X-ray acquisition module 106 may be selected based on the detection result (such as the existence of an imaging target in suitable position to an X-ray acquisition module) in step 2220. Merely by way of example, if the existence is detected by an X-ray acquisition module of a vertical configuration, such as when an imaging target stands next to the vertical stand 2201, then the detection result may be transmitted to the control module 103, and then the vertical configuration X-ray acquisition module may be selected. Similarly, if the existence is detected by X-ray acquisition module of a horizontal configuration, such as when an imaging target lies horizontally on an imaging bed component 2203, then the detection result may be transmitted to the control module 103, and then the horizontal configuration X-ray acquisition module may be selected. If neither configuration detects the presence of an imaging target in suitable position, a free-style configuration X-ray acquisition module may be selected. The free-style X-ray acquisition module may assume any angle with respect to the imaging space or target. Additionally or alternatively, when a free-style configuration is selected, an end user (e.g., a doctor) may manual select a suitable X-ray acquisition module 106 and/or adjust position and angle of corresponding system components.

In step 2230, the selected X-ray acquisition module 106 may be activated. As used herein, activating a selected X-ray acquisition module indicates that one or more units (not shown) of the selected X-ray acquisition module may be activated, such as but not limited to the ionization chamber (not shown), and/or the filter grid (not shown), etc. During the activation process, one or more acquisition parameters may be set or adjusted, such as duration, sensitivity, current, voltage, temperature, etc. Particularly, after the activation process, the process may proceed to step 2240 to determine whether an X-ray detector is ready, such as whether an X-ray detector is at a suitable location relative to the imaging target for X-ray image acquisition of the imaging target. In some embodiments, only one X-ray detector may be present in the system (see, e.g., FIGS. 2-B, 3-A, 3-B). In other embodiments, more than one X-ray detectors may be present in the system. For example, both the vertical and horizontal X-ray acquisition modules may include their own independent X-ray detector (see, e.g., FIG. 2-A).

If no X-ray detector is ready in step 2240, the process may be paused and an exposure may be prohibited in step 2250. If an X-ray detector is ready, the process may be continued. For example, one or more parameters for the exposure may be set in step 2260. The exposure parameters may include exposure current, exposure voltage, exposure duration, dosage or the like, or a combination thereof. Also, an exposure controller may be used (as described in FIGS. 9-11). Subsequently an exposure may be performed in step 2270 and corresponding X-ray images may be obtained. The structures and functions described above are not exhaustive and are not limiting; numerous other changes, substitutions, variations, alterations, and modifications may be ascertained to one skilled in the art and it is intended that the present disclosure encompasses all such changes, substitutions, variations, alterations, and modifications as falling within the scope of the appended claims. For example, in step 2260, the exposure parameter may be set by the system default and may be transmitted from the processing module 105. In another example, if an exposure parameter does not conform to a specific rule set by the system default, an alarm signal may be generated to warn an end user (e.g., a doctor) to stop the process of the system.

Figure 23:
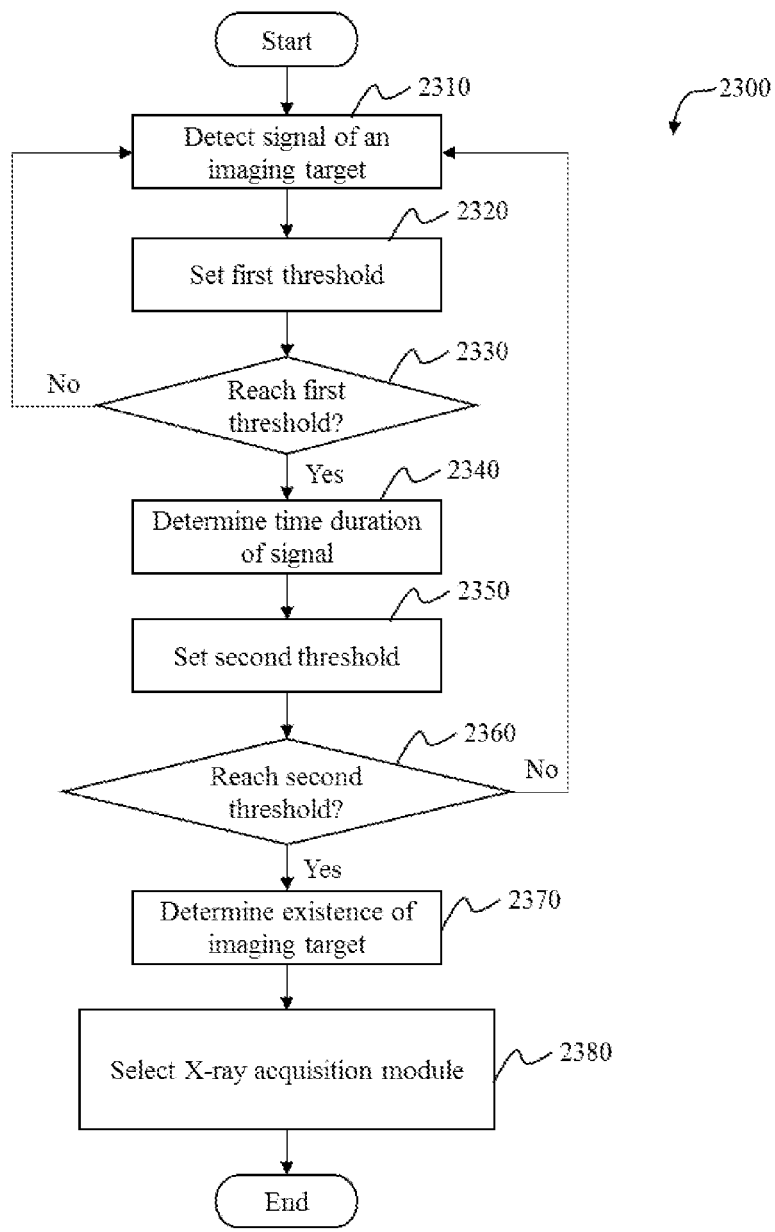
FIG. 23 illustrates an exemplary process for detecting existence of an imaging target according to some embodiments of the present disclosure.

FIG. 23 provides an exemplary process for detecting an imaging target according to some embodiments of the present disclosure. In step 2310, a signal may be detected or sensed form an imaging target. In some embodiments, the signal may be an optical signal acquired by an infrared sensing method. In some embodiments, the signal may be an image signal acquired by a portrait discrimination method. In some embodiments, the signal may be a reflected electromagnetic wave signal acquired by a radar device. In step 2320, a first threshold regarding the detected signal may be set. The first threshold may be set by the system default, or may be set by an end user (e.g., a doctor). In some embodiments, the first threshold may be a single value, or may be a value range. In some embodiments, the first threshold may be a reference signal, or may be one or more feature points of the reference signal. Merely by way of example, the first threshold may be a value of infrared radiation quantity. In step 2330, a comparison may be performed as to whether the detected signal reaches the first threshold. If the answer is "Yes," a time duration of the detected signal may be determined in step 2340. As used herein, the time duration refers to a time period during which the detected signal persists. If the answer is "No," the process may return to step 2310 to start a new detection process.

After the time duration of the detected signal is determined, a second threshold may be set in step 2350. The second threshold may be a single value of a duration time, or may be a value range. The second threshold may be set by the system default, or may be set by an end user (e.g., a doctor). In step 2360, a comparison between the determined time duration of the detected signal with the second threshold may be performed. If the time duration does not reach the second threshold, the process may return to step 2310 to start a new detection process. If the duration time reaches or exceeds the second threshold, the process may determine that an imaging target exists (step 2370). As used herein, existence of an imaging target indicates that an imaging target is in a suitable position relative to an X-ray acquisition module for imaging. In step 2380, an X-ray acquisition module may be selected based on the detected existence of the imaging target. The selection process will be described in further details in relation to FIG. 24 below.

Figure 24:
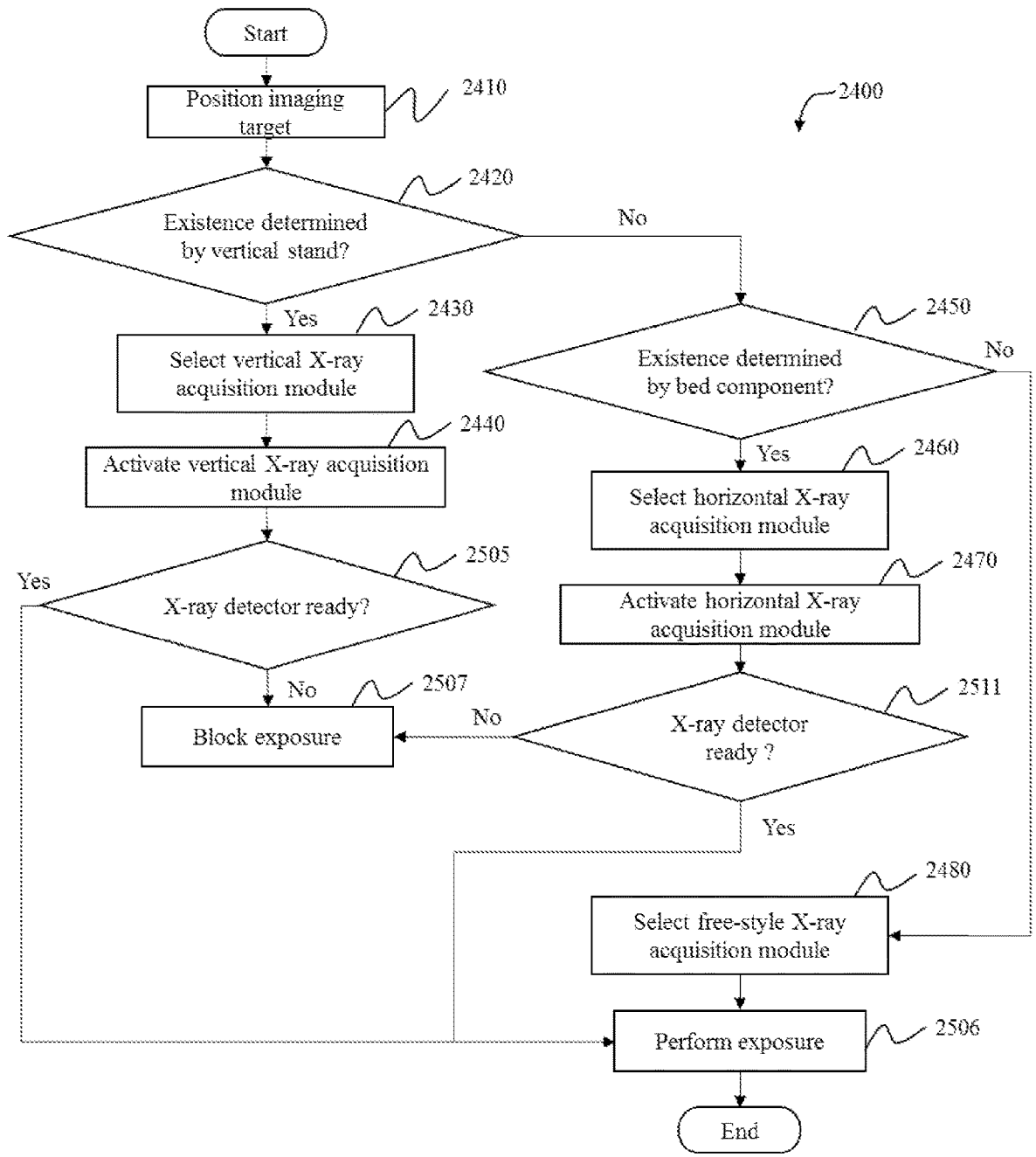
FIG. 24 illustrates an exemplary process for selecting an X-ray acquisition module according to the present disclosure.

FIG. 24 provides an exemplary process for selecting an X-ray acquisition module according to the present disclosure. Particularly, the process and the steps illustrated in FIG. 24 may be one embodiment of the selection process illustrated by FIG. 22 and related descriptions. In step 2410, an imaging target may be positioned in place for imaging. After the positioning of the imaging target, the process may proceed to step 2420 to determine whether existence of the imaging target is detected by the vertical configuration X-ray acquisition module. The detection may be performed by the first detection unit 2203 installed on the vertical stand 2201 (see FIG. 2-A). As described in FIG. 2-A, the first detection unit 2203 may be an infrared sensor, or may be any sensor or device that can be used for detecting the existence of an imaging target. The detection of existence of an imaging target may be performed according to step 2210 in FIG. 22. If existence of the imaging target is determined by the detection unit 2203 on the vertical stand 2201, the detection may indicate that an imaging target is in a suitable position for imaging by the vertical configuration. Thus, an X-ray acquisition module of the vertical configuration may be selected in step 2430.

In some embodiments, the selection may be performed by the control module 103 based on the sensing result. In some embodiments, the selection may be performed automatically by the system while receiving the sensing result. In some embodiments, the selection may be performed by an end user (e.g., a doctor). Subsequently the selected X-ray acquisition module of the vertical configuration may be activated in step 2440. In some embodiments, in step 2505, whether an X-ray detector on the vertical stand is ready is determined. As described in relation to FIG. 22, an X-ray detector is ready indicates that an X-ray detector is at a suitable location relative to the imaging target for X-ray image acquisition of the imaging target. If the answer is "Yes," an exposure may be performed in step 2506. If the answer is "No," the exposure may be prohibited in step 2507. In some embodiments, detecting whether an X-ray detector is ready (step 2505) is not performed.

If existence of an imaging target is not detected by the detection unit 2203 on the vertical stand 2201 in step 2420, the process may proceed to step 2450 to determine whether existence of an imaging target is detected by the second detection unit 2205 on the bed component 2203 (see, FIG. 2-A). The second detection 2205 may be an infrared sensor, or may be any sensor that can be used for detecting the existence of an imaging target. If the answer is "Yes," it may indicate that an imaging target in a suitable position for imaging by the horizontal configuration. Thus, X-ray acquisition module of the horizontal configuration may be selected in step 2460. Subsequently, the selected horizontal configuration X-ray acquisition module may be activated in step 2470. In step 2511, whether an X-ray detector on the bed component 2203 is ready is determined. If the answer in Step 2511 is "Yes," then the process may proceed to step 2506 to perform an exposure. In some embodiments, detecting whether an X-ray detector is ready (step 2511) is not performed.

If existence of an imaging target is also not detected nearby the bed component in step 2450, the process may proceed to step 2480 to select X-ray acquisition module of a free-style configuration. As described above, the free-style configuration acquisition module may assume any angle with respect to the imaging space or target. Additionally or alternatively, when a free-style configuration is selected, an end user (e.g., a doctor) may manual select a suitable X-ray acquisition module 106 and/or adjust position and angle of corresponding system components. FIG. 24 only provides one embodiment of the selection process for an X-ray acquisition module, it should be noted that other than the embodiment, some other embodiments in which one or more new steps may be added or one or more steps may be removed may also implement the operations or functions of the disclosed digital radiography system.

According to one aspect of the present disclosure, provided herein are methods for controlling X-ray exposure, which aims to improve safety and efficiency of the operation of the digital radiography system.

Figure 25:
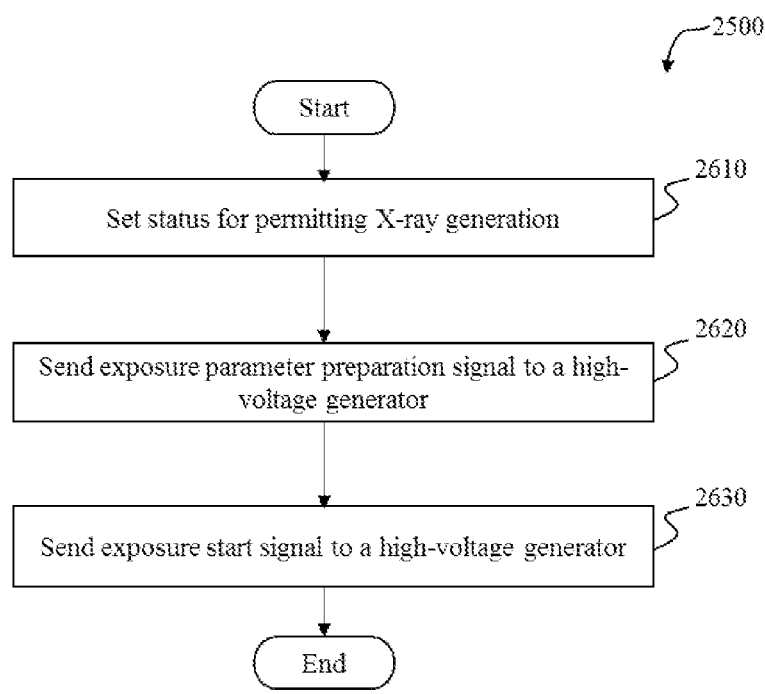
FIG. 25 illustrates an exemplary process for controlling X-ray exposure according to the present disclosure.

FIG. 25 provides an exemplary process 2500 for controlling X-ray exposure according to the present disclosure. In some embodiments, the process may be performed by the exposure controller 910 (see, FIGS. 9-11 and related descriptions).

In step 2610, the process may set a status for permitting X-ray generation. The status for permitting X-ray generation may be set by software mechanism, or by a hardware mechanism, or both. In some embodiments, the status for permitting X-ray generation may be set by pressing the switch 1001 on the exposure control unit 905 (see, e.g., FIG. 9).

In step 2620, the process 2500 may send an exposure parameter preparation signal to a high-voltage generator 1203. The exposure parameter preparation signal may be a continuous signal, or may be a discrete signal. The exposure parameter preparation signal may be a pulse signal of a certain frequency. In some embodiments, the exposure parameter preparation signal may be sent by pressing down the first gear 1004 of the exposure controller 910 (see e.g., FIG. 9).

In step 2630, the process may send an exposure start signal to a high-voltage generator 1203. The exposure start signal may be a continuous signal, or may be a discrete signal. The exposure start signal may be a pulse signal of a certain frequency. The exposure start signal and the exposure preparation signal may be generated by a same component, unit, and/or module. In some embodiments, sending the exposure start signal is after sending the exposure parameter preparation signal in order to enhance security of the imaging target. In some embodiments, the exposure start signal may be generated by the pressing down the second gear 1005 of the exposure controller 910 (see e.g., FIG. 9).

The structures and functions described above are not exhaustive and are not limiting; numerous other changes, substitutions, variations, alterations, and modifications may be ascertained to one skilled in the art and it is intended that the present disclosure encompasses all such changes, substitutions, variations, alterations, and modifications as falling within the scope of the appended claims. For example, step 2620 may not be necessary in some embodiments. In another example, the exposure start signal may be sent simultaneously with the exposure parameter preparation signal.

What is claimed is:

1. A method using in a digital radiography system for X-ray imaging, wherein the digital radiography system comprises an X-ray generation module, an X-ray acquisition module, a support module including a vertical stand and a bed component, a power supply module, and a control module, wherein one or more of said modules comprise at least one moving component, the method comprising:
   detecting existence of an imaging target in a vertical configuration or a horizontal configuration, wherein one or more of said modules form the vertical configuration or the horizontal configuration, the vertical configuration comprises a vertical X-ray acquisition module coupled to the vertical stand, and the horizontal configuration comprises a horizontal X-ray acquisition module coupled to the bed component;
   activating, by the control module, the vertical X-ray acquisition module in response to a detection that the imaging target exists in the vertical configuration; and
   activating, by the control module, the horizontal X-ray acquisition module in response to a detection that the imaging target exists in the horizontal configuration.

2. The method according to claim 1, further comprising:
   timing the detected existence; and
   activating, by the control module, the vertical or horizontal configuration if the detected existence persists for a threshold time.

3. The method according to claim 1, wherein the vertical X-ray acquisition module and the horizontal X-ray acquisition module each comprises an X-ray detector, an ionization chamber and a filter grid.

4. The method according to claim 3, further comprising:
   activating, by the control module, the ionization chamber and the filter grid of the selected vertical or horizontal configuration.

5. The method according to claim 3, further comprising:
   determining, by the control module, if the X-ray detector of the activated vertical or horizontal configuration is ready for image acquisition.

6. The method according to claim 1, wherein the one or more of said modules further form a free-style configuration, the method further comprising:
   activating, by the control module, the free-style configuration if the existence of the imaging target is not detected in the vertical configuration and the horizontal configuration.

7. The method according to claim 1, wherein the existence of the imaging target in a vertical configuration or a horizontal configuration is detected by an infrared detector.

8. The method according to claim 1, further comprising:
   obtaining a sensing result relating to the at least one moving component; and
   controlling, by the control module, motion of the at least one moving component based on said sensing result.

9. The method according to claim 1, wherein said sensing result comprises positional information including a distance between the moving component and a nearby object, the method further comprising:
   comparing said distance to a threshold; and
   adjusting, by the control module, speed of the motion, route of the motion, or both, when the distance exceeds the threshold.

10. The method according to claim 9, wherein the at least one moving component is an X-ray detector, an X-ray tube, a ceiling suspension unit, a beam limiting device, or a tube stand, and wherein the tube stand connects the X-ray tube and the ceiling suspension unit.

11. A digital radiography system comprising an X-ray generation module, an X-ray acquisition module, a support module including a vertical stand and a bed component, a power supply module and a control module, wherein one or more of said modules comprise at least one moving component;
   one or more of said modules form a vertical configuration or a horizontal configuration;
   the vertical configuration comprises a vertical X-ray acquisition module coupled to the vertical stand;
   the horizontal configuration comprises a horizontal X-ray acquisition module coupled to the bed component;
   the control module comprises a detection unit configured to detect existence of an imaging target in the vertical configuration or the horizontal configuration;
   the control module is further configured to activate the vertical X-ray acquisition module in response to a detection that the imaging target exists in the vertical configuration; and
   the control module is further configured to activate the horizontal X-ray acquisition module in response to a detection that the imaging target exists in the horizontal configuration.

12. The digital radiography system according to claim 11, wherein the control module is further configured to
   time the detected existence, and
   activate the vertical or horizontal configuration if the detected existence persists for a threshold time.

13. The digital radiography system according to claim 11, wherein the vertical X-ray acquisition module and the horizontal X-ray acquisition module each comprises an X-ray detector, an ionization chamber and a filter grid.

14. The digital radiography system according to claim 13, wherein the control module is further configured to activate the ionization chamber and the filter grid of the selected vertical or horizontal configuration.

15. The digital radiography system according to claim 13, wherein the control module is further configured to determine if the X-ray detector of the activated vertical or horizontal configuration is ready for image acquisition.

16. The digital radiography system according to claim 11, wherein the one or more of said modules further form a free-style configuration, and the control module is further configured to activate the free-style configuration if the existence of the imaging target is not detected in the vertical configuration and the horizontal configuration.

17. The digital radiography system according to claim 11, wherein the detection unit is an infrared detector.

18. The digital radiography system according to claim 11, wherein the control module is configured to control motion of the at least one moving component based on positional information of the moving component.

19. The digital radiography system according to claim 18, wherein
   the positional information includes a distance between the moving component and a nearby object; and
   the control module is further configured to
   compare said distance to a threshold; and
   adjust speed of the motion, route of the motion, or both, when the distance exceeds the threshold.

20. The digital radiography system according to claim 19, wherein the at least one moving component is an X-ray detector, an X-ray tube, a ceiling suspension unit, a beam limiting device, or a tube stand, and wherein the tube stand connects the X-ray tube and the ceiling suspension unit.

* * * * *